(12) United States Patent
Ullrich, Jr. et al.

(10) Patent No.: US 8,480,749 B2
(45) Date of Patent: *Jul. 9, 2013

(54) FRICTION FIT AND VERTEBRAL ENDPLATE-PRESERVING SPINAL IMPLANT

(75) Inventors: Peter F. Ullrich, Jr., Neenah, WI (US); Chad J. Patterson, Port Washington, WI (US); Jennifer M. Schneider, Germantown, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,904

(22) Filed: Jun. 6, 2012

(65) Prior Publication Data
US 2012/0239150 A1 Sep. 20, 2012

Related U.S. Application Data

(63) Continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)

(52) U.S. Cl.
USPC ........ 623/17.16; 623/17.11; 606/90; 606/100

(58) Field of Classification Search
USPC .................. 623/17.11–17.16; 606/90, 100
See application file for complete search history.

(56) References Cited

U.S. PATENT DOCUMENTS

| | | | |
|---|---|---|---|
| 4,314,876 A | 2/1982 | Kremer et al. |
| 4,904,261 A | 2/1990 | Dove et al. |
| 5,015,247 A | 5/1991 | Michelson |
| 5,071,437 A | 12/1991 | Steffee |
| 5,258,098 A | 11/1993 | Wagner et al. |
| 5,306,309 A | 4/1994 | Wagner et al. |
| 5,425,772 A | 6/1995 | Brantigan |

(Continued)

FOREIGN PATENT DOCUMENTS

| | | |
|---|---|---|
| EP | 0599419 | 6/1994 |
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Eduardo C Robert
*Assistant Examiner* — Julianna N Harvey
(74) *Attorney, Agent, or Firm* — Stradley Ronon Stevens & Young, LLP

(57) ABSTRACT

An interbody spinal implant including a body having a top surface, a bottom surface, opposing lateral sides, opposing anterior and posterior portions, a substantially hollow center, a single vertical aperture, and a roughened surface topography on at least the top surface. The posterior portion has a generally rounded nose profile, and has a shorter height than the anterior portion such that the spinal implant comprises a lordotic angle for aligning the spine of a patient. The junctions of the top and bottom surfaces and the anterior portion comprise a sharp edge to resist expulsion of the spinal implant upon implantation.

24 Claims, 14 Drawing Sheets

U.S. PATENT DOCUMENTS

| | | | |
|---|---|---|---|
| 5,443,514 A | 8/1995 | Steffee |
| 5,456,723 A | 10/1995 | Steinemann et al. |
| 5,507,815 A | 4/1996 | Wagner et al. |
| 5,571,188 A | 11/1996 | Ellingsen et al. |
| 5,603,338 A | 2/1997 | Beaty |
| 5,609,635 A | 3/1997 | Michelson |
| 5,702,449 A | 12/1997 | McKay |
| 5,766,252 A | 6/1998 | Henry et al. |
| 5,776,199 A | 7/1998 | Michelson |
| 5,860,973 A | 1/1999 | Michelson |
| 5,863,201 A | 1/1999 | Lazzara et al. |
| 5,876,453 A | 3/1999 | Beaty |
| 5,885,079 A | 3/1999 | Niznick |
| 5,888,224 A | 3/1999 | Beckers et al. |
| 5,922,029 A | 7/1999 | Wagner et al. |
| 5,968,098 A | 10/1999 | Winslow |
| 5,984,922 A | 11/1999 | McKay |
| 6,033,582 A | 3/2000 | Lee et al. |
| 6,039,762 A | 3/2000 | McKay |
| 6,059,829 A | 5/2000 | Schlaepfer et al. |
| 6,080,158 A | 6/2000 | Lin |
| 6,123,705 A | 9/2000 | Michelson |
| 6,143,032 A | 11/2000 | Schafer et al. |
| 6,183,255 B1 | 2/2001 | Oshida |
| 6,193,757 B1 | 2/2001 | Foley et al. |
| 6,193,762 B1 | 2/2001 | Wagner et al. |
| 6,241,770 B1 | 6/2001 | Michelson |
| 6,241,771 B1 | 6/2001 | Gresser et al. |
| 6,245,108 B1 | 6/2001 | Biscup |
| 6,296,664 B1 | 10/2001 | Middleton |
| 6,302,914 B1 | 10/2001 | Michelson |
| 6,342,074 B1 | 1/2002 | Simpson |
| 6,350,283 B1 | 2/2002 | Michelson |
| 6,387,130 B1 | 5/2002 | Stone et al. |
| 6,395,031 B1 | 5/2002 | Foley et al. |
| 6,423,095 B1 | 7/2002 | Van Hoeck et al. |
| 6,432,140 B1 | 8/2002 | Lin |
| 6,447,544 B1 | 9/2002 | Michelson |
| 6,458,159 B1 | 10/2002 | Thalgott |
| 6,478,823 B1 | 11/2002 | Michelson |
| 6,482,233 B1 | 11/2002 | Aebi et al. |
| 6,485,517 B1 | 11/2002 | Michelson |
| 6,491,723 B1 | 12/2002 | Beaty |
| 6,558,424 B2 | 5/2003 | Thalgott |
| 6,579,318 B2 | 6/2003 | Varga et al. |
| 6,592,624 B1 | 7/2003 | Fraser et al. |
| 6,599,322 B1 | 7/2003 | Amrich et al. |
| 6,610,089 B1 | 8/2003 | Liu et al. |
| 6,620,332 B2 | 9/2003 | Amrich |
| 6,635,086 B2 | 10/2003 | Lin |
| 6,652,765 B1 | 11/2003 | Beaty |
| 6,676,703 B2 | 1/2004 | Biscup |
| 6,702,855 B1 | 3/2004 | Steinemann et al. |
| 6,719,794 B2 | 4/2004 | Gerber et al. |
| 6,726,720 B2 | 4/2004 | Ross et al. |
| 6,730,127 B2 | 5/2004 | Michelson |
| 6,740,118 B2 | 5/2004 | Eisermann et al. |
| 6,743,231 B1 | 6/2004 | Gray et al. |
| 6,758,849 B1 | 7/2004 | Michelson |
| 6,833,006 B2 | 12/2004 | Foley et al. |
| 6,890,355 B2 | 5/2005 | Michelson |
| 6,902,581 B2 | 6/2005 | Walkenhorst et al. |
| 6,911,249 B2 | 6/2005 | Wagner et al. |
| 6,923,810 B1 | 8/2005 | Michelson |
| 6,974,480 B2 | 12/2005 | Messerli et al. |
| 6,981,975 B2 | 1/2006 | Michelson |
| 7,018,418 B2 | 3/2006 | Amrich et al. |
| 7,041,137 B2 | 5/2006 | Fulton et al. |
| 7,044,972 B2 | 5/2006 | Mathys, Jr. et al. |
| 7,048,870 B1 | 5/2006 | Ellingsen et al. |
| 7,060,073 B2 | 6/2006 | Frey et al. |
| 7,066,961 B2 | 6/2006 | Michelson |
| 7,087,085 B2 | 8/2006 | Steinemann et al. |
| 7,112,224 B2 | 9/2006 | Lie et al. |
| 7,128,760 B2 | 10/2006 | Michelson |
| 7,137,997 B2 | 11/2006 | Paul |
| 7,144,428 B2 | 12/2006 | Anitua |
| 7,166,129 B2 | 1/2007 | Michelson |
| 7,169,183 B2 | 1/2007 | Liu et al. |
| D539,934 S | 4/2007 | Blain |
| 7,201,775 B2 | 4/2007 | Gorensek et al. |
| D541,940 S | 5/2007 | Blain |
| 7,220,280 B2 | 5/2007 | Kast et al. |
| 7,223,289 B2 | 5/2007 | Trieu et al. |
| 7,226,480 B2 | 6/2007 | Thalgott |
| 7,238,186 B2 | 7/2007 | Zdeblick et al. |
| 7,244,275 B2 | 7/2007 | Michelson |
| 7,255,698 B2 | 8/2007 | Michelson |
| 7,288,093 B2 | 10/2007 | Michelson |
| 7,311,734 B2 | 12/2007 | Van Hoeck et al. |
| D564,095 S | 3/2008 | Blain |
| 7,347,873 B2 | 3/2008 | Paul et al. |
| D566,276 S | 4/2008 | Blain |
| 7,368,065 B2 | 5/2008 | Yang et al. |
| 7,410,501 B2 | 8/2008 | Michelson |
| 7,501,073 B2 | 3/2009 | Wen et al. |
| 7,503,933 B2 | 3/2009 | Michelson |
| 7,517,363 B2 | 4/2009 | Rogers et al. |
| D599,019 S | 8/2009 | Pimenta et al. |
| 7,569,074 B2 | 8/2009 | Eisermann et al. |
| 7,608,107 B2 | 10/2009 | Michelson |
| 7,615,078 B2 | 11/2009 | White et al. |
| 7,655,042 B2 | 2/2010 | Foley et al. |
| 7,662,186 B2 * | 2/2010 | Bagga et al. ............... 623/17.16 |
| 7,662,190 B2 | 2/2010 | Steinemann et al. |
| 7,744,612 B2 | 6/2010 | Blain |
| 7,846,183 B2 | 12/2010 | Blain |
| 7,901,462 B2 | 3/2011 | Yang et al. |
| 7,998,172 B2 | 8/2011 | Blain |
| 8,062,304 B2 | 11/2011 | Blain et al. |
| 8,100,955 B2 | 1/2012 | Blain et al. |
| 8,142,355 B2 | 3/2012 | Blain et al. |
| 8,172,854 B2 | 5/2012 | Blain et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0087212 A1 * | 7/2002 | James et al. ............... 623/17.11 |
| 2002/0161443 A1 * | 10/2002 | Michelson ................ 623/17.11 |
| 2002/0173854 A1 | 11/2002 | Amrich |
| 2003/0014116 A1 * | 1/2003 | Ralph et al. ............... 623/17.16 |
| 2003/0105527 A1 | 6/2003 | Bresina |
| 2003/0109928 A1 | 6/2003 | Pasquet et al. |
| 2003/0125739 A1 | 7/2003 | Bagga et al. |
| 2003/0153975 A1 | 8/2003 | Byrd, III et al. |
| 2003/0181980 A1 | 9/2003 | Berry et al. |
| 2003/0181981 A1 | 9/2003 | Lemaire |
| 2003/0187506 A1 | 10/2003 | Ross et al. |
| 2004/0117020 A1 | 6/2004 | Frey et al. |
| 2004/0127993 A1 * | 7/2004 | Kast et al. ................. 623/17.16 |
| 2004/0153154 A1 | 8/2004 | Dinkelacker |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0131416 A1 * | 6/2005 | Jansen et al. .................... 606/86 |
| 2005/0147942 A1 | 7/2005 | Hall |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |

| | | | |
|---|---|---|---|
| 2007/0118223 A1 | 5/2007 | Allard et al. | |
| 2007/0233247 A1 | 10/2007 | Schwab | |
| 2007/0233248 A1 | 10/2007 | Schwab et al. | |
| 2007/0260320 A1 | 11/2007 | Peterman et al. | |
| 2007/0270956 A1 | 11/2007 | Heinz | |
| 2007/0282441 A1 | 12/2007 | Stream et al. | |
| 2007/0288028 A1 | 12/2007 | Gorensek et al. | |
| 2008/0014243 A1 | 1/2008 | Ellingsen et al. | |
| 2008/0071380 A1 | 3/2008 | Sweeney | |
| 2008/0077171 A1 | 3/2008 | Blain et al. | |
| 2008/0195209 A1 | 8/2008 | Garcia et al. | |
| 2008/0221689 A1 | 9/2008 | Chaput et al. | |
| 2008/0262623 A1 | 10/2008 | Bagga et al. | |
| 2008/0269764 A1 | 10/2008 | Blain et al. | |
| 2008/0269806 A1 | 10/2008 | Zhang et al. | |
| 2009/0005784 A1 | 1/2009 | Blain et al. | |
| 2009/0024132 A1 | 1/2009 | Blain et al. | |
| 2009/0082819 A1 | 3/2009 | Blain et al. | |
| 2009/0088800 A1 | 4/2009 | Blain et al. | |
| 2009/0088853 A1 | 4/2009 | Ogilvie et al. | |
| 2009/0132048 A1 | 5/2009 | Denzer | |
| 2009/0182432 A1 | 7/2009 | Zdeblick et al. | |
| 2009/0187247 A1 | 7/2009 | Metcalf, Jr. et al. | |
| 2009/0204152 A1 | 8/2009 | Blain | |
| 2009/0234362 A1 | 9/2009 | Blain et al. | |
| 2009/0264928 A1 | 10/2009 | Blain | |
| 2009/0276049 A1 | 11/2009 | Weiland | |
| 2009/0312837 A1 | 12/2009 | Eisermann et al. | |
| 2010/0121385 A1 | 5/2010 | Blain et al. | |
| 2010/0173264 A1 | 7/2010 | Fredriksson et al. | |
| 2010/0204798 A1 | 8/2010 | Gerbec et al. | |
| 2010/0218854 A1 | 9/2010 | Garcia Saban et al. | |
| 2010/0228288 A1 | 9/2010 | Blain | |
| 2010/0249937 A1 | 9/2010 | Blain et al. | |
| 2010/0274286 A1 | 10/2010 | Blain et al. | |
| 2011/0040301 A1 | 2/2011 | Blain et al. | |
| 2011/0082503 A1 | 4/2011 | Blain | |
| 2011/0224796 A1 | 9/2011 | Weiland et al. | |
| 2011/0230970 A1 | 9/2011 | Lynn et al. | |
| 2011/0233169 A1 | 9/2011 | Mayfield et al. | |
| 2012/0009341 A1 | 1/2012 | Noh et al. | |
| 2012/0046695 A9 | 2/2012 | Blain | |
| 2012/0123424 A1 | 5/2012 | Blain et al. | |
| 2012/0123548 A1 | 5/2012 | Lynn et al. | |
| 2012/0136443 A1 | 5/2012 | Wentzel | |
| 2012/0149991 A1 | 6/2012 | Blain et al. | |
| 2012/0158056 A1 | 6/2012 | Blain | |
| 2012/0239151 A1 | 9/2012 | Ulrich, Jr. | |

FOREIGN PATENT DOCUMENTS

| | | |
|---|---|---|
| EP | 1449544 | 8/2004 |
| EP | 2386274 | 11/2011 |
| JP | 08010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004041131 | 5/2004 |
| WO | 2006081843 | 8/2006 |
| WO | 2006116306 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants 2011; 26:115-122.

ISA, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (2009) 736-742.

Meirelles, et al., "The Effect of Chemical and Nanotopographical Modifications on the Early Stages of Osseointegration", Int. J. Oral Maxillofac. Implants 2008; 23:641-647.

Supplemenatry Partial European Search Report issued Sep. 27, 2011, for EP 06 75 9086.

Supplementary Partial European Search Report issued Aug. 19, 2011, for EP 06 75 9086.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

* cited by examiner

FRICTION FIT AND VERTEBRAL ENDPLATE-PRESERVING SPINAL IMPLANT

CROSS REFERENCE TO RELATED APPLICATIONS

This application is a continuation-in-part of U.S. patent application Ser. No. 12/151,198, filed on May 5, 2008, which is a continuation-in-part of U.S. patent application Ser. No. 11/123,359, filed on May 6, 2005, and issued as U.S. Pat. No. 7,662,186. The contents of both prior applications are incorporated by reference in this document, in their entirety and for all purposes.

FIELD OF THE INVENTION

The invention relates generally to interbody spinal implants and methods of using such implants and, more particularly, to an implant having one or more openings of predetermined sizes and shapes to achieve design trade offs depending upon a particular application.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This location is not the preferable seating position for an implant system, however, because only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence (defined as sinking or settling) into the softer cancellous bone of the vertebral body may arise from such improper seating.

In contrast, open ring-shaped cage implant systems are generally shaped to mimic the anatomical contour of the vertebral body. Traditional ring-shaped cages are generally comprised of allograft bone material, however, harvested from the human femur. Such allograft bone material restricts the usable size and shape of the resultant implant. For example, many of these femoral ring-shaped cages generally have a medial-lateral width of less than 25 mm. Therefore, these cages may not be of a sufficient size to contact the strong cortical bone, or apophyseal rim, of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Still further, other traditional non-allograft ring-shaped cage systems may be size-limited due to varied and complex supplemental implant instrumentation which may obstruct the disc space while requiring greater exposure of the operating space. These supplemental implant instrumentation systems also generally increase the instrument load upon the surgeon.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Nevertheless, traditional implantation practices often do not preserve critical bone structures such as vertebral endplates during the surgical procedure. In some cases, the implant devices themselves necessitate removal of bone and were not designed or implanted with the intent to preserve critical bone structures during or after implantation.

Traditional interbody spinal implants generally do not seat properly on the preferred structural bone located near the apophyseal rim of the vertebral body, which is primarily composed of preferred dense subchondral bone. Accordingly, there is a need in the art for interbody spinal implants which better utilize the structurally supportive bone of the apophyseal rim.

In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

There are three traditional end-plate preparation methods. The first is aggressive end-plate removal with box-chisel types of tools to create a nice match of end-plate geometry with implant geometry. In the process of aggressive end-plate removal, however, the end-plates are typically destroyed.

Such destruction means that the load-bearing implant is pressed against soft cancellous bone and the implant tends to subside.

The second traditional end-plate preparation method preserves the end-plates by just removing cartilage with curettes. The end-plates are concave; hence, if a flat implant is used, the implant is not very stable. Even if a convex implant is used, it is very difficult to match the implant geometry with the end-plate geometry, as the end-plate geometry varies from patient-to-patient and on the extent of disease.

The third traditional end-plate preparation method uses threaded fusion cages. The cages are implanted by reaming out corresponding threads in the end-plates. This method also violates the structure.

Traditional anterior spinal fusion devices can also be difficult to implant. Some traditional implants with teeth have sharp edges. These edges can bind to the surrounding soft tissue during implantation, creating surgical challenges.

Typically, secondary instrumentation is used to keep the disc space distracted during implantation. The use of such instrumentation means that the exposure needs to be large enough to accommodate the instrumentation. If there is a restriction on the exposure size, then the maximum size of the implant available for use is correspondingly limited. The need for secondary instrumentation for distraction during implantation also adds an additional step or two in surgery. Still further, secondary instrumentation may sometimes over-distract the annulus, reducing the ability of the annulus to compress a relatively undersized implant. The compression provided by the annulus on the implant is important to maintain the initial stability of the implant.

For anterior spinal surgery, there are traditionally three trajectories of implants: anterior, antero-lateral, and lateral. Each approach has its advantages and drawbacks. Sometimes the choice of the approach is dictated by surgeon preference, and sometimes it is dictated by patient anatomy and biomechanics. A typical traditional implant has design features to accommodate only one or two of these approaches in a single implant, restricting intra-operative flexibility.

Other challenges raised by traditional devices find their source in the conventional materials of construction. Typical devices are made of PEEK or cadaver bone. Materials such as PEEK or cadaver bone do not have the structural strength to withstand impact loads required during implantation and may fracture during implantation.

PEEK is an abbreviation for polyetherether-ketone, a high-performance engineering thermoplastic with excellent chemical and fatigue resistance plus thermal stability. With a maximum continuous working temperature of 480° F., PEEK offers superior mechanical properties. Superior chemical resistance has allowed PEEK to work effectively as a metal replacement in harsh environments. PEEK grades offer chemical and water resistance similar to PPS (polyphenylene sulfide), but can operate at higher temperatures. PEEK materials are inert to all common solvents and resist a wide range of organic and inorganic liquids. Thus, for hostile environments, PEEK is a high-strength alternative to fluoropolymers.

The use of cadaver bone has several drawbacks. The shapes and sizes of the implants are restricted by the bone from which the implant is machined. Cadaver bone carries with it the risk of disease transmission and raises shelf-life and storage issues. In addition, there is a limited supply of donor bone and, even when available, cadaver bone inherently offers inconsistent properties due to its variability. Finally, as mentioned above, cadaver bone has insufficient mechanical strength for clinical application.

Traditional implants can migrate and expel out of the disc space, following the path through which the implant was inserted. Typical implants are either "threaded" into place, or have "teeth" which are designed to prevent expulsion. Both options can create localized stress risers in the end-plates, increasing the chances of subsidence. The challenge of preventing implant expulsion is especially acute for PEEK implants, because the material texture of PEEK is very smooth and "slippery."

Subsidence of the implant is a complex issue and has been attributed to many factors. Some of these factors include aggressive removal of the end-plate; an implant stiffness significantly greater than the vertebral bone; smaller sized implants which tend to seat in the center of the disc space, against the weakest region of the end-plates; and implants with sharp edges which can cause localized stress fractures in the end-plates at the point of contact. The most common solution to the problem of subsidence is to choose a less stiff implant material. This is why PEEK and cadaver bone have become the most common materials for spinal fusion implants. PEEK is softer than cortical bone, but harder than cancellous bone.

Cadaver bone implants are restricted in their size by the bone from which they are machined. Their wall thickness also has to be great to create sufficient structural integrity for their desired clinical application. These design restrictions do not leave much room for filling the bone graft material into cortical bone implants. The exposure-driven limitations on implant size narrow the room left inside the implant geometry for bone grafting even for metal implants. Such room is further reduced in the case of PEEK implants because their wall thickness needs to be greater as compared to metal implants due to structural strength needs.

For fusion to occur, the bone graft packed inside the implant needs to be loaded mechanically. Typically, however, the stiffness of the implant material is much greater than the adjacent vertebral bone and takes up a majority of the mechanical loads, "shielding" the bone graft material from becoming mechanically loaded. The most common solution is to choose a less stiff implant material. Again, this is why PEEK and cadaver bone have become the most common materials for spinal fusion implants. As noted above, although harder than cancellous bone, PEEK is softer than cortical bone.

In most cases, the typical fusion implant is not able to incorporate with the vertebral bone, even years after implantation. Such inability persists despite the use of a variety of different materials to construct the implants. There is a perception that cadaver bone is resorbable and will be replaced by new bone once it resorbs. Hedrocel is a composite material composed of carbon and tantalum, an inert metal, that has been used as a material for spinal fusion implants. Hedrocel is designed to allow bone in-growth into the implant. In contrast, PEEK has been reported to become surrounded by fibrous tissue which precludes it from incorporating with surrounding bone. There have also been reports of the development of new bio-active materials which can incorporate into bone. The application of such bio-active materials has been limited, however, for several reasons, including biocompatibility, structural strength, and lack of regulatory approval.

For implants made out of metal, the metal prevents adequate radiographic visualization of the bone graft. Hence it is difficult to assess fusion, if it is to take place. PEEK is radiolucent. Traditional implants made of PEEK need to have radiographic markers embedded into the implants so that implant position can be tracked on an X-ray. Cadaver bone has some radiopacity and does not interfere with radiographic assessment as much as metal implants.

The requirements of spinal surgery dictate that manufacturers provide implants of various foot-prints, and several heights in each foot-print. This requirement means that the manufacturer needs to carry a significant amount of inventory of implants. Because there are so many different sizes of implants, there are setup costs involved in the manufacture of each different size. The result is increased implant costs, which the manufacturers pass along to the end users by charging high prices for spinal fusion implants.

SUMMARY OF THE INVENTION

The invention is directed to interbody spinal implants and to methods of using such implants. The implants can be inserted, using methods of the invention, from a variety of vantages, including anterior, antero-lateral, and lateral implantation. The spinal implant is preferably adapted to be inserted into a prepared disc space via a procedure which does not destroy the vertebral end-plates, or contacts the vertebral end-plates only peripherally, allowing the intact vertebral end-plates to deflect like a diaphragm under axial compressive loads generated due to physiologic activities and pressurize the bone graft material disposed inside the spinal implant.

In some aspects, a spinal implant is generally oval-shaped in transverse cross-section, and comprises a top surface, a bottom surface, opposing lateral sides, and opposing anterior and posterior portions. The posterior portion defines a leading end for insertion into a disc space, has a generally rounded nose profile, and has a shorter height than the anterior portion such that the implant comprises a lordotic angle capable of aligning the spine. The top surface, the bottom surface, or both have a roughened surface topography adapted to grip bone and inhibit migration of the implant. The lengths between the top surface and the posterior portion, the bottom surface and the posterior portion, the top surface and the lateral sides, and the bottom surface and the lateral sides include generally rounded or blunt and radiused intersections. The junction of the top and/or bottom surface and the anterior portion comprises an expulsion-resistant edge to resist pullout of the implant from the spine.

The spinal implant is preferably substantially hollow and comprises a centrally disposed vertical aperture extending from the top surface to the bottom surface, defining a transverse rim in the top and bottom surfaces having a greater first thickness in the area of the posterior portion than a second thickness in the area of the anterior portion to improve utilization of the vertebrae, and having a maximum width at its center, between the opposing lateral sides, and tapering inwardly from the center to each of its ends, one end proximate the anterior portion and the other end proximate the posterior portion. The substantially hollow portion may contain a bone graft material adapted to facilitate the formation of a solid fusion column within the spine. The bone graft material may be cancellous autograft bone, allograft bone, demineralized bone matrix (DBM), porous synthetic bone graft substitute, bone morphogenic protein (BMP), or a combination thereof.

The spinal implant may be fabricated from a metal. A preferred metal is titanium. The spinal implant may be fabricated from a non-metallic material, non-limiting examples of which include polyetherether-ketone, hedrocel, ultra-high molecular weight polyethylene, and combinations thereof. The spinal implant may be fabricated from both a metal and a non-metallic material, including a composite thereof. For example, a composite may be formed, in part, of titanium and, in part, of polyetherether-ketone, hedrocel, ultra-high molecular weight polyethylene, or combinations thereof.

The anterior portion may be substantially flat and adapted to receive impact from an implant tool. The anterior portion may comprise an opening for achieving one or more of the following functions: being adapted to engage a delivery device, facilitating delivery of bone graft material to the substantially hollow center, enhancing visibility of the implant, and providing access to the bone graft material.

The invention also features systems that include such interbody spinal implants. The systems may comprise an implant and a distractor. The systems may further comprise a rasp. The systems may further comprise an implant holder capable of engaging an opening on the anterior portion of the spinal implant. The systems may further comprise a bone graft material, non-limiting examples of which include cancellous autograft bone, allograft bone, demineralized bone matrix (DBM), porous synthetic bone graft substitute, bone morphogenic protein (BMP), or a combination thereof.

The distractor of the systems may comprise a top surface, a bottom surface, opposing lateral sides, and opposing anterior and posterior portions, with the posterior portion defining a leading end for insertion first into a disc space, having a generally rounded nose profile, and having a shorter height than the anterior portion such that the distractor comprises a lordotic angle. The distractor is adapted to be inserted into a prepared disc space via a procedure which does not destroy the vertebral end-plates, or contacts the vertebral end-plates only peripherally.

The rasp of the systems may comprise a top surface, a bottom surface, opposing lateral sides, opposing anterior and posterior portions, and a plurality of teeth having a tip facing the anterior portion. The teeth preferably extend laterally across the top surface, the bottom surface, or the top and bottom surfaces of the rasp. The posterior portion of the rasp preferably defines a leading end for insertion first into a disc space, has a generally rounded nose profile, and has a shorter height than the anterior portion such that the rasp comprises a lordotic angle.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 11 shows a side view of the embodiment of the interbody spinal implant shown in

FIG. 9;

DETAILED DESCRIPTION OF THE INVENTION

Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the invention, allow for improved visualization of implant seating and fusion assessment. Interbody spinal implants, as now taught, may also facilitate osteointegration with the surrounding living bone.

Anterior interbody spinal implants in accordance with certain aspects of the invention can be preferably made of a durable material such as stainless steel, stainless steel alloy, titanium, or titanium alloy, but can also be made of other durable materials such as, but not limited to, polymeric, ceramic, and composite materials. For example, certain embodiments of the invention may be comprised of a biocompatible, polymeric matrix reinforced with bioactive fillers, fibers, or both. Certain embodiments of the invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor during implantation.

Figure 1:
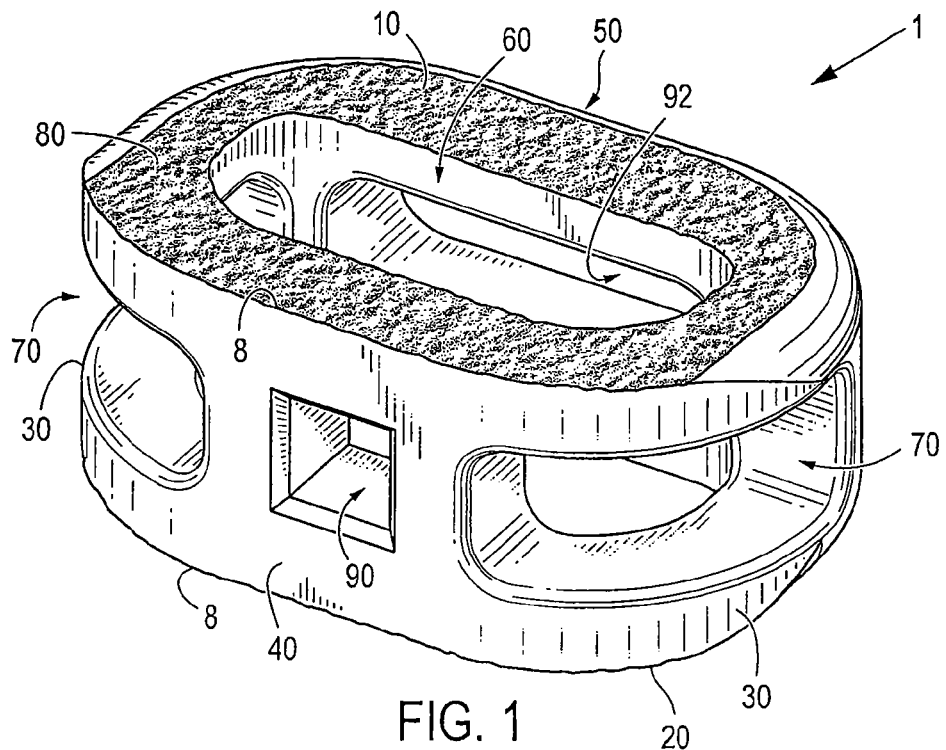
FIG. 1 shows a perspective view of an embodiment of the interbody spinal implant having a generally oval shape and roughened surface topography on the top surface.
Figure 9:
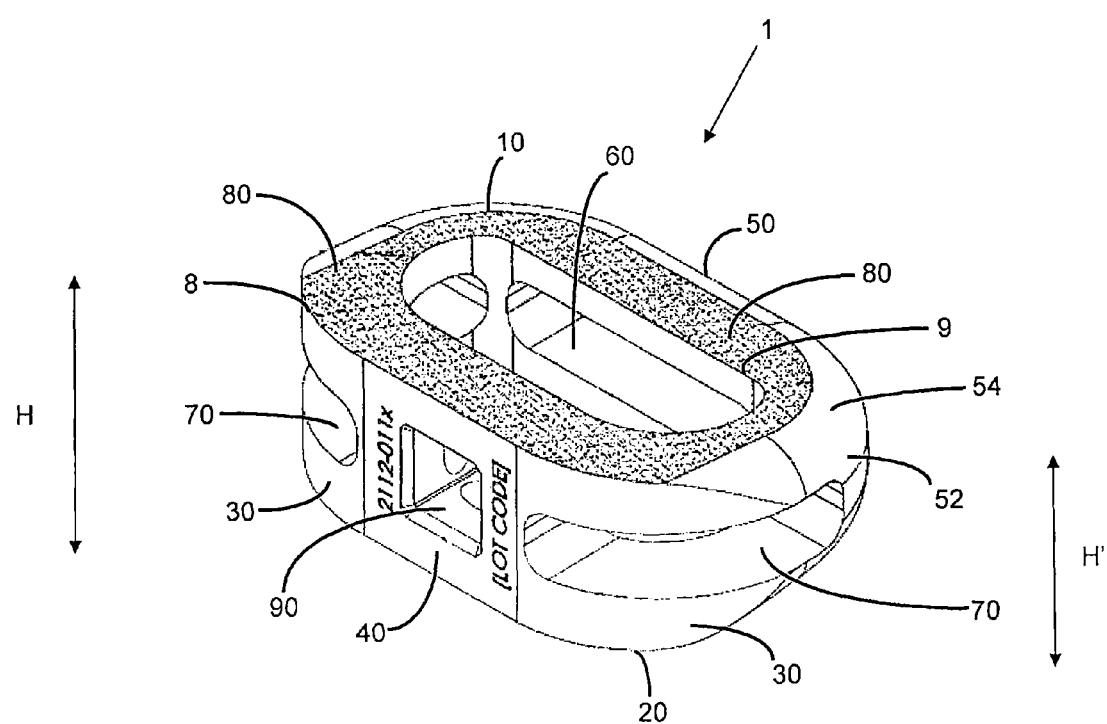
FIG. 9 shows an isometric view of an embodiment of the interbody spinal implant having a generally oval shape, a roughened surface topography, and rounded edges about the proximal surface.

Referring now to the drawing, in which like reference numbers refer to like elements throughout the various figures that comprise the drawing, FIG. 1 shows a perspective view of a first embodiment of the interbody spinal implant 1 especially well adapted for use in an ALIF procedure. FIG. 9 shows a perspective view of an alternative embodiment of the interbody spinal implant 1.

The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. The roughened topography 80, however, is distinct from the teeth provided on the surfaces of some conventional devices.

Figure 2:
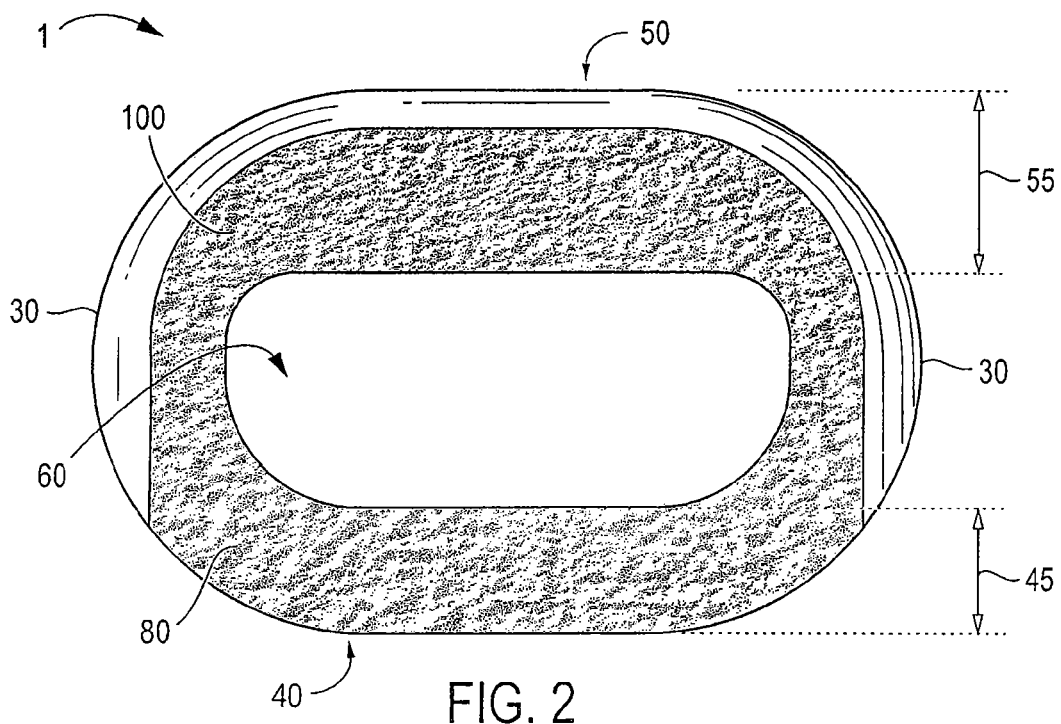
FIG. 2 depicts a top view of the interbody spinal implant.

In some aspects, the interbody spinal implant 1 is substantially hollow and has a generally oval-shaped transverse cross-sectional area with smooth, rounded, or both smooth and rounded lateral sides 30 and posterior-lateral corners 52. A substantially hollow implant 1 includes an implant 1 having at least about 33% of the interior volume of the implant 1 vacant. The implant 1 includes at least one vertical aperture 60 that extends the entire height of the implant body. As illustrated in the top view of FIG. 2 and FIG. 10, the vertical aperture 60 may further define a transverse rim 100 having a greater posterior portion thickness 55 than an anterior portion thickness 45.

In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40. Some studies have challenged the characterization of the posterior endplate bone as weaker.

It is generally believed that the surface of an implant determines its ultimate ability to integrate into the surrounding living bone. Without being limited to any particular theory or mechanism of action, it is believed that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface. Still further, it appears that these cells attach more readily to relatively rough surfaces rather than smooth surfaces. In this manner, a surface may be bioactive due to its ability to facilitate cellular attachment and osteointegration. The surface roughened topography 80 may better promote the osteointegration of the implant 1. The surface roughened topography 80 may also better grip the vertebral endplate surfaces and inhibit implant migration of the implant 1 upon placement and seating in a patient.

Accordingly, the implant 1 further includes the roughened topography 80 on at least a portion of its top 10 and bottom 20 surfaces for gripping adjacent bone and inhibiting migration of the implant 1. FIG. 1 and FIG. 9 show roughened topography 80 on embodiments of the implant 1.

The roughened topography 80 may be obtained through a variety of techniques including, without limitation, chemical etching, shot peening, plasma etching, laser etching, or abrasive blasting (such as sand or grit blasting). In at least one embodiment, the interbody spinal implant 1 may be comprised of titanium, or a titanium alloy, having the surface roughened topography 80. The surfaces of the implant 1 are preferably bioactive.

In a preferred embodiment of the invention, the roughened topography 80 is obtained via the repetitive masking and chemical or electrochemical milling processes described in U.S. Pat. Nos. 5,258,098; 5,507,815; 5,922,029; and 6,193,762. Each of these patents is incorporated in this document by reference. Where the invention employs chemical etching, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.53 mm. Interbody spinal implants 1, in accordance with some preferred embodiments of the invention, may be comprised of titanium, or a titanium alloy, having an average surface roughness of about 100 μm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles).

The implant 1 may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim.

Figure 3:
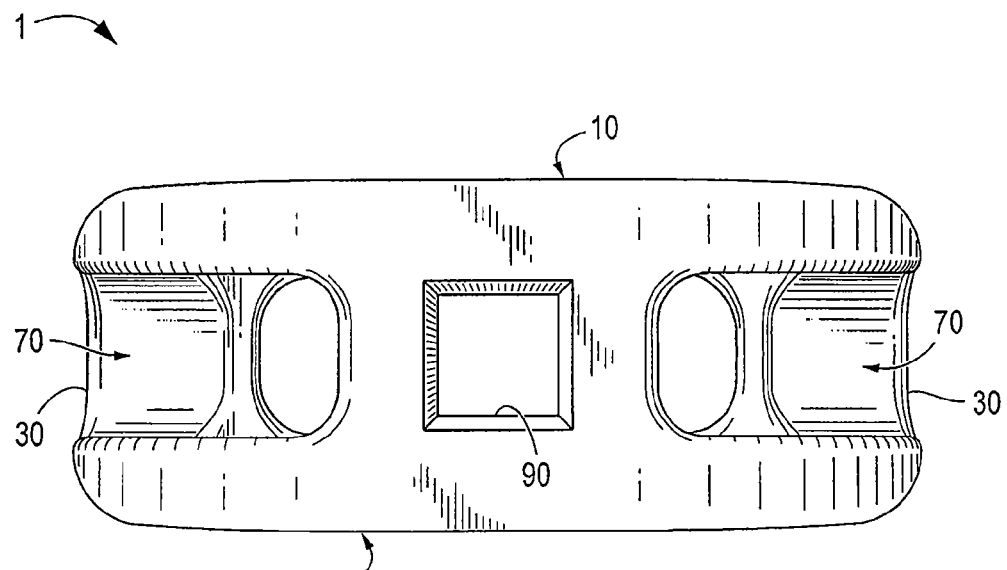
FIG. 3 depicts an anterior view of the interbody spinal implant.
Figure 4:
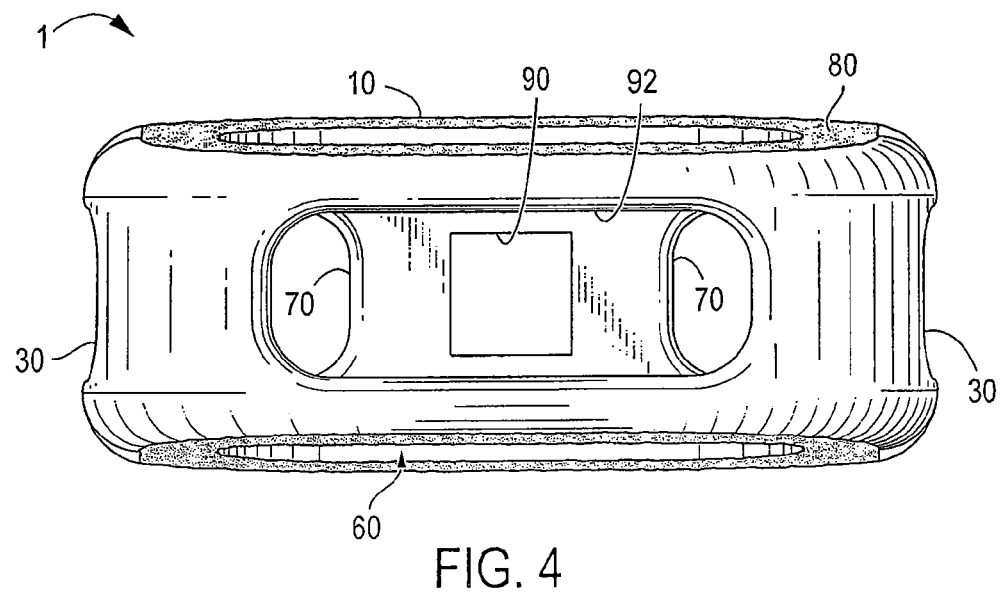
FIG. 4 depicts a posterior view of the interbody spinal implant.

FIG. 3 depicts an anterior view, and FIG. 4 depicts a posterior view, of an embodiment of the interbody spinal implant 1. As illustrated in FIG. 1, FIG. 3, and FIG. 9, the implant 1 has an opening 90 in the anterior portion 40. As illustrated in FIGS. 3 and 4, in one embodiment the posterior portion 50 has a similarly shaped opening 90. The embodiment shown in FIG. 9 may also have a posterior portion 50 with a similarly shaped opening 90 (not shown). In some aspects, as illustrated in FIG. 1 and in FIG. 9, only the anterior portion 40 has the opening 90 while the posterior portion 50 has an alternative opening 92 (which may have a size and shape different from the opening 90).

The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement.

Figure 6:
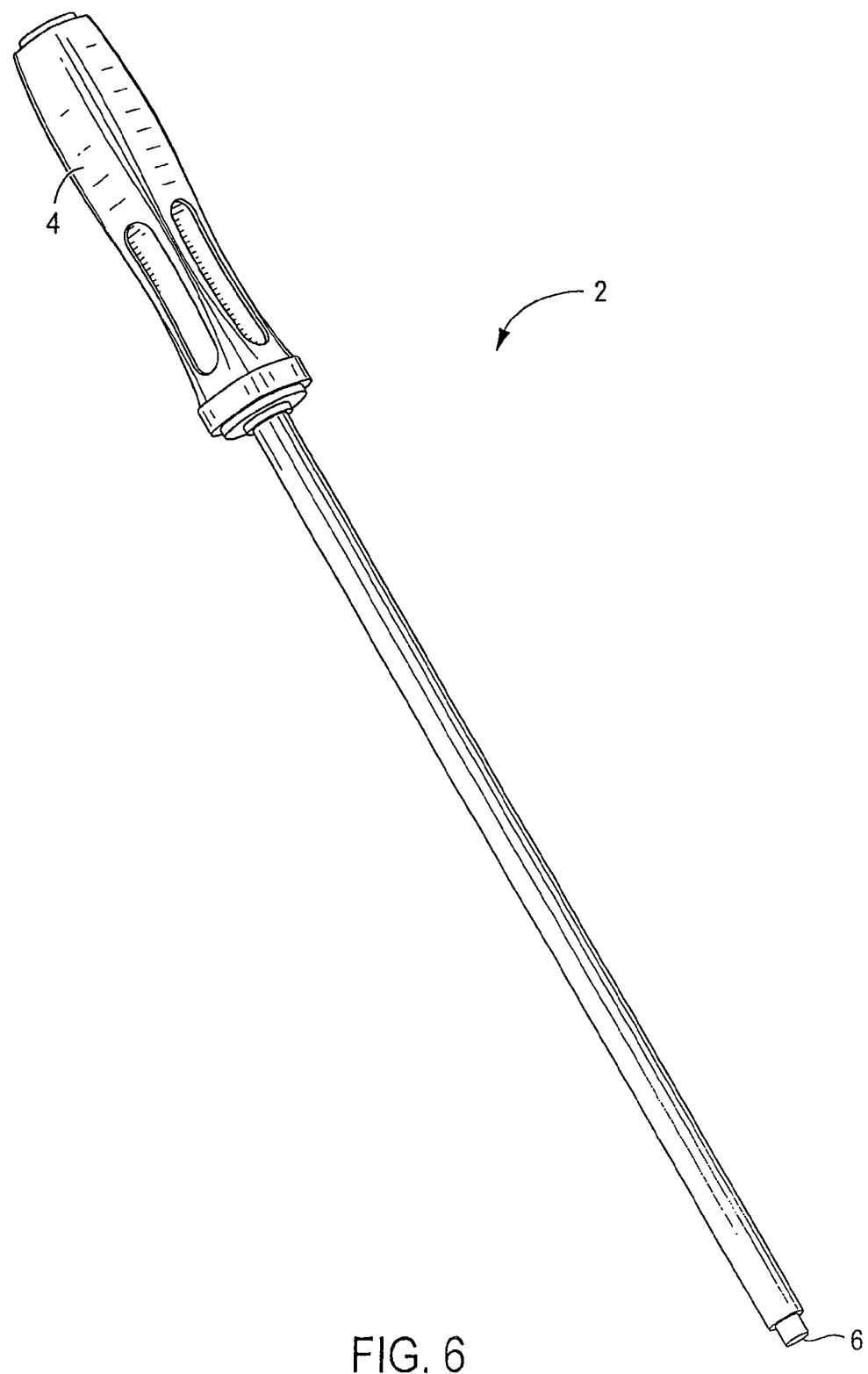
FIG. 6 shows an exemplary surgical tool (implant holder) to be used with certain embodiments of the interbody spinal implant.

FIG. 6 shows an exemplary surgical tool, specifically an implant holder 2, to be used with certain embodiments of the interbody spinal implant 1. Typically, the implant holder 2 has a handle 4 that the caretaker can easily grasp and an end 6 that engages the opening 90. The end 6 may be threaded to engage corresponding threads in the opening 90. The size and shape of the opening 90 can be varied to accommodate a variety of tools. Thus, although the opening 90 is substantially square as illustrated in FIGS. 1, 3, 4, and 9, other sizes and shapes are feasible.

Figure 5A:
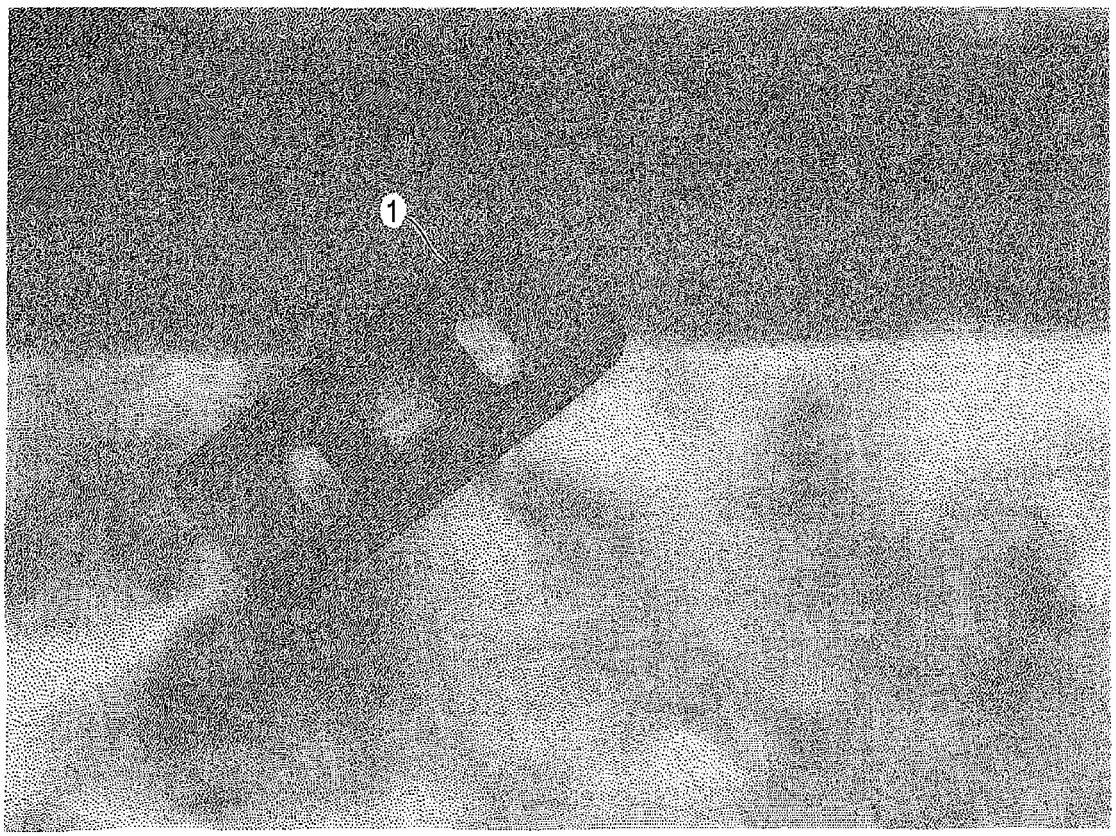
FIG. 5A depicts a first post-operative radiograph showing visualization of an embodiment of the interbody spinal implant.
Figure 5B:
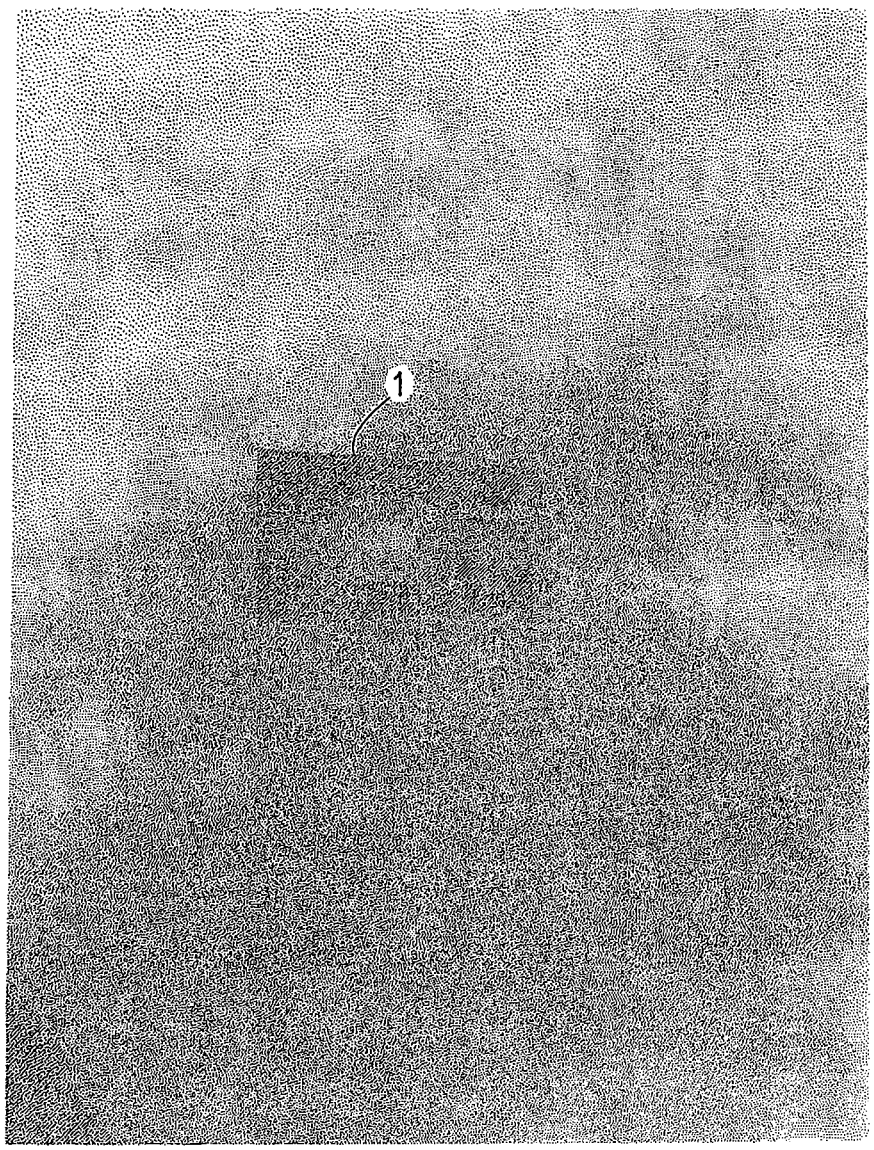
FIG. 5B depicts a second post-operative radiograph showing visualization of an embodiment of the interbody spinal implant.
Figure 5C:
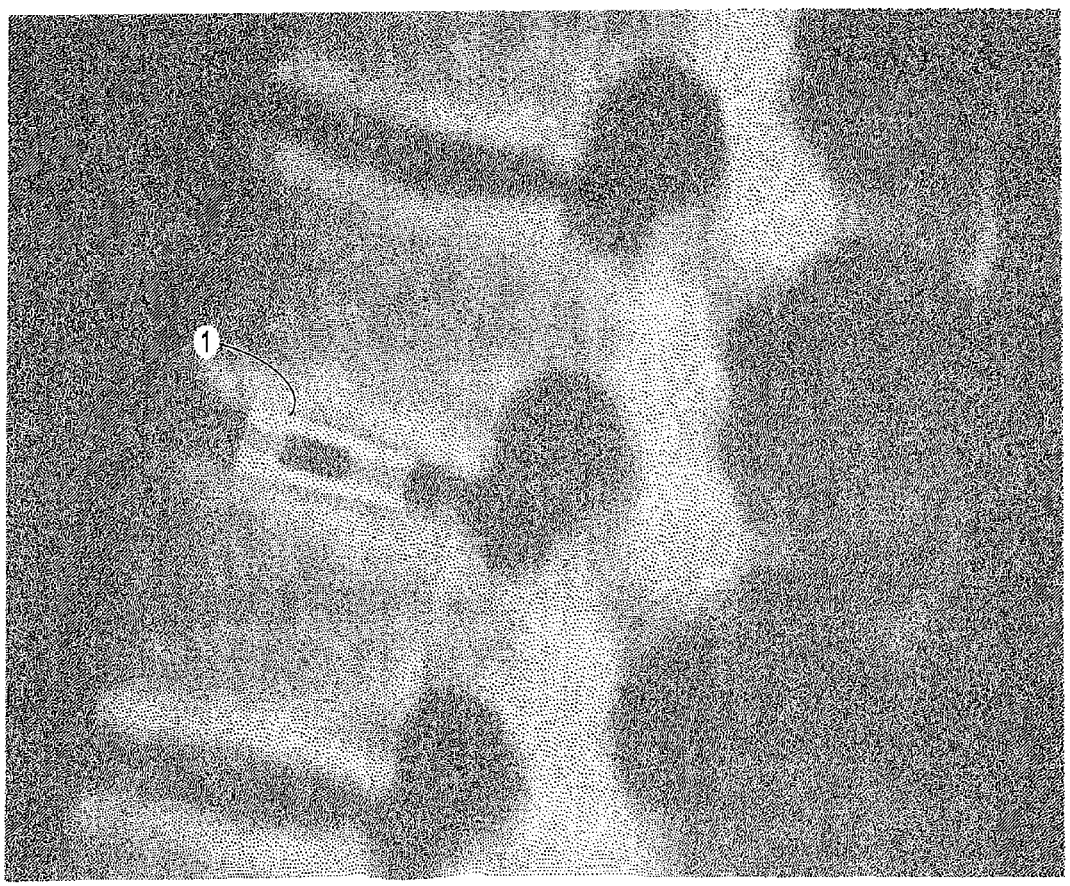
FIG. 5C depicts a third post-operative radiograph showing visualization of an embodiment of the interbody spinal implant.

The implant 1 may further include at least one transverse aperture 70 that extends the entire transverse length of the implant body. As shown in FIGS. 5A-5C and in FIG. 9, the at least one transverse aperture 70 may provide improved visibility of the implant 1 during surgical procedures to ensure proper implant placement and seating, and may also improve post-operative assessment of implant fusion. Still further, the substantially hollow area defined by the implant 1 may be filled with cancellous autograft bone, allograft bone, DBM, porous synthetic bone graft substitute, BMP, or combinations of these materials (collectively, bone graft materials), to facilitate the formation of a solid fusion column within the spine of a patient.

Figure 11A:
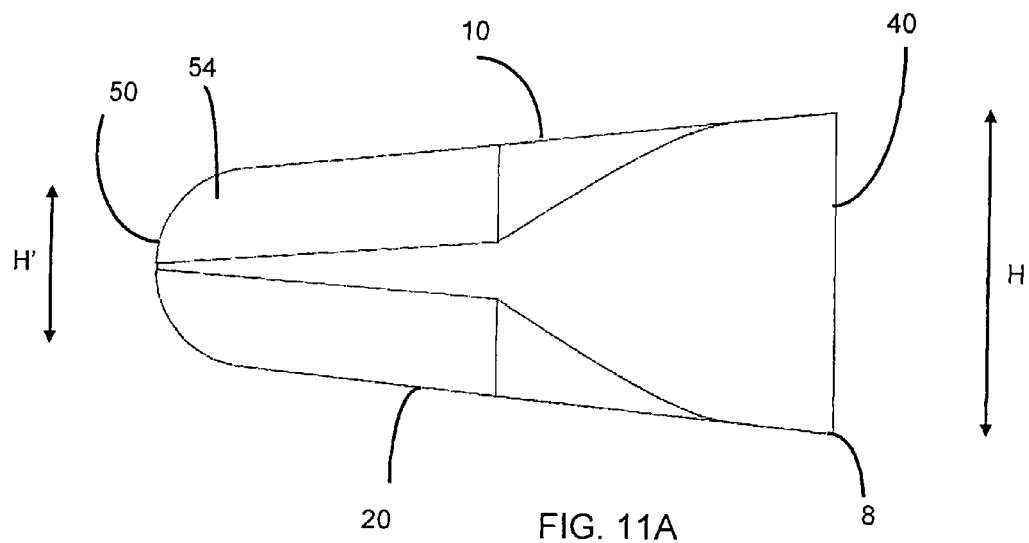
Figure 11B:
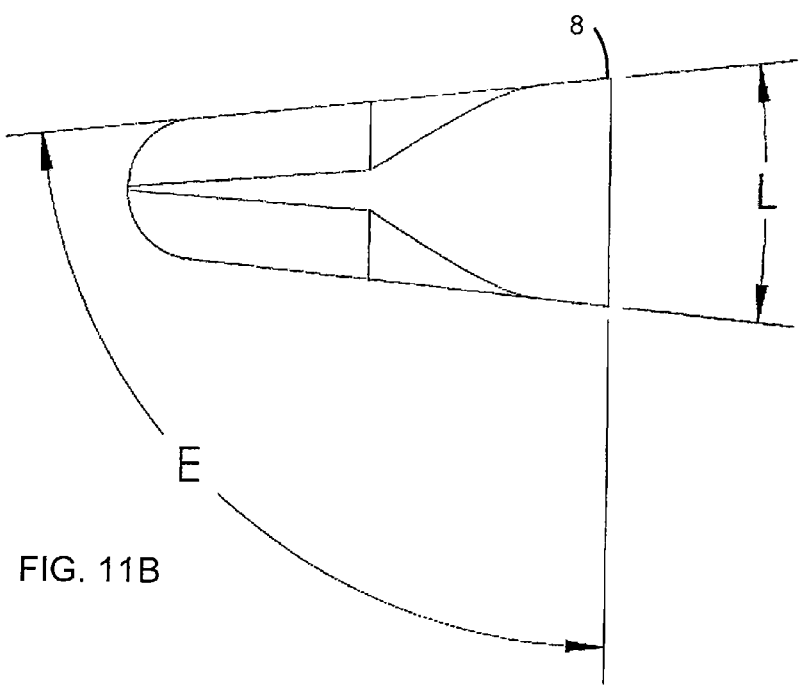

The anterior portion 40, or trailing edge, of the implant 1 is preferably generally greater in height than the opposing posterior portion 50. Accordingly, the implant 1 may comprise a lordotic-angle, e.g., may be wedge-shaped to facilitate sagittal alignment. Thus, for example, the anterior portion 40 of the implant 1 may comprise a height H that is larger than the height H' of the posterior portion 50, as shown in FIG. 9 and FIG. 11A. The anterior portion 40 height H and posterior portion 50 height H' may vary, and may vary independently, in order to accommodate different lordotic angles in the spines of different patients. FIG. 11A and FIG. 11B. In some aspects, the implant 1 may better compensate for less supportive bone such as that which may be found in the posterior regions of the vertebral endplate.

The anterior portion 40 height H and the posterior portion 50 height H' may each independently be from about 5 mm to about 75 mm. In preferred aspects, the height H and the height H' may each independently be from about 8 mm to about 20 mm. Thus, for example, either the height H or the height H' may be selected from about 5 mm, about 8 mm, about 10 mm, about 12 mm, about 14 mm, about 16 mm, about 18 mm, about 20 mm, about 22 mm, about 24 mm, about 25 mm, about 28 mm, about 30 mm, about 33 mm, about 35 mm, about 38 mm, about 40 mm, about 43 mm, about 45 mm, about 48 mm, about 50 mm, about 53 mm, about 55 mm, about 58 mm, about 60 mm, about 63 mm, about 65 mm, about 68 mm, about 70 mm, about 75 mm, or about 80 mm.

The difference in the anterior portion 40 height H and the posterior portion 50 height H' may result in a lordotic angle L of from about 3 degrees to about 15 degrees, from the horizontal plane of the implant 1. In preferred aspects, the implant 1 comprises an angle of about 4 degrees, about 5 degrees, about 6 degrees, about 7 degrees, about 8 degrees, about 9 degrees, about 10 degrees, about 11 degrees, or about 12 degrees. Angles of lordosis of about 4 degrees, about 6 degrees, about 7 degrees, or about 12 degrees are highly preferred.

The posterior portion 50 of the interbody implant 1, preferably including the posterior-lateral corners 52, may also be highly radiused, thus allowing for ease of implantation into the disc space. Thus, the posterior portion 50 may have a generally blunt nosed profile, including a generally rounded profile, for example, as shown in FIG. 9 and in FIG. 11A. The posterior portion edges 54, including the top and bottom edges and lateral corner edges of the posterior portion 50, are preferably generally rounded, and are preferably smooth.

As illustrated in FIG. 1 and FIG. 9, the anterior portion 40 of the implant 1 is substantially flat. Thus, the anterior portion 40 provides a face that can receive impact from a tool, such as a surgical hammer, to force the implant 1 into position.

Figure 10:
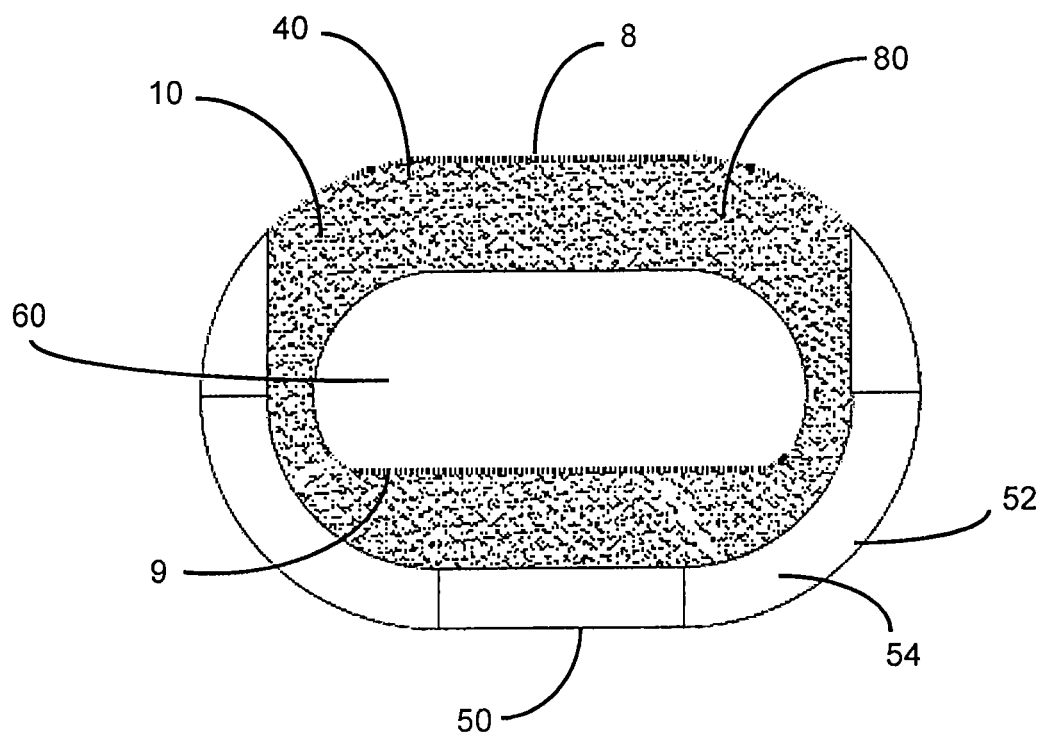
FIG. 10 shows a top view of the embodiment of the interbody spinal implant shown in FIG. 9, and further shows anti-expulsion edges.

In some aspects, the implant 1 has a first expulsion-resistant edge 8 where the anterior portion 40 meets the top surface 10, where the anterior portion 40 meets the bottom surface 20, or in both locations; see, e.g., FIG. 1, FIG. 9, and FIG. 10. The edge 8 may be sharp or sharpened, or may comprise a blade, a lip, a ridge, or a barb. The expulsion-resistant edges 8 (top and/or bottom) function to resist movement of the implant 1 out from the spine once the implant 1 has been inserted into position.

The implant 1 may also comprise a second expulsion-resistant edge 9 on at least the posterior edge 62 of the vertical aperture 60, as shown in FIG. 10. The second expulsion-resistant edge 9 may be present where the vertical aperture 60 intersects the top surface 10, where the vertical aperture 60 intersects the bottom surface 20, or in both locations. The edge 9 may be sharp or sharpened, or may comprise a blade, a lip, a ridge, or a barb. The expulsion-resistant edges 9 (top and/or bottom) function to resist movement of the implant 1 out from the spine once the implant 1 has been inserted into position, and may be used in addition to or in lieu of the expulsion-resistant edge 8 on the anterior portion 40. In some aspects, the first expulsion-resistant edge 8 and the second expulsion-resistant edge 9 function to resist movement of the implant 1 out from the spine once it the implant 1 has been inserted into position, and their movement resistance may be additive, though their respective contributions to resistance may not be equal.

The expulsion-resistant edge 8 may comprise an anti-expulsion edge angle E, for example, as shown in FIG. 11B. The anti-expulsion edge angle E may be from about 80 degrees to about 100 degrees. In preferred aspects, the anti-expulsion edge angle E may be measured by taking into account the lordosis angle L of the implant 1. In highly preferred aspects, the anti-expulsion edge angle E is measured by subtracting half of the lordotic angle L from 90. For example, where the lordosis angle L of the implant 1 is 12 degrees, the anti-expulsion edge angle E is 84 degrees (90−(12×0.5)). The anti-expulsion edge angle E may be about 80 degrees, about 81 degrees, about 82 degrees, about 83 degrees, about 84 degrees, about 85 degrees, about 86 degrees, about 86.5 degrees, about 87 degrees, about 88 degrees, or about 89 degrees.

Certain embodiments of the invention are particularly suited for use during interbody spinal implant procedures (or vertebral body replacement procedures) and may act as a final distractor during implantation, thus minimizing the instrument load upon the surgeon. For example, in such a surgical procedure, the spine may first be exposed via an anterior approach and the center of the disc space identified. The disc space is then initially prepared for implant insertion by removing vertebral cartilage. Soft tissue and residual cartilage may then also be removed from the vertebral endplates.

Vertebral distraction may be performed using trials of various-sized embodiments of the interbody spinal implant 1. The determinatively sized interbody implant 1 may then be inserted in the prepared disc space for final placement. The distraction procedure and final insertion may also be performed under fluoroscopic guidance. The substantially hollow area within the implant body may optionally be filled, at least partially, with bone fusion-enabling materials such as, without limitation, cancellous autograft bone, allograft bone, DBM, porous synthetic bone graft substitute, BMP, or combinations of those materials. Such bone fusion-enabling material may be delivered to the interior of the interbody spinal implant 1 using a delivery device mated with the opening 90 in the anterior portion 40 of the implant 1. The interbody spinal implant 1 may be generally larger than those currently known in the art, and therefore have a correspondingly larger hollow area which may deliver larger volumes of fusion-enabling bone graft material. The bone graft material may be delivered such that it fills the full volume, or less than the full volume, of the implant interior and surrounding disc space appropriately.

The spinal implant 1 is easier to use than ring-shaped cages made of allograft bone material. For example, it is easier to prepare the graft bed, relative to the allograft cage, for the spinal implant 1. And ring allograft cages typically are not sufficiently wide to be implanted on the apophasis. The spinal implant 1 offers a large internal area for bone graft material and does not require graft preparation, cutting, or trimming. The central aperture 60 of the spinal implant 1 can be filled with cancellous allograft, porous synthetic bone graft substitute, or BMP. The process of healing the bone can proceed by intra-membranous ossification rather than the much slower process of enchondral ossification.

The spinal implant 1 is generally stronger than allograft cages. In addition, the risk of osteolysis (or, more generally, disease transmission) is minimal with the spinal implant 1 because titanium is osteocompatible. The titanium of the spinal implant 1 is unaffected by BMP; there have been reports that BMP causes resorption of allograft bone.

In contrast to conventional treaded titanium cages, which offer little bone-to-bone contact (about 9%), the spinal implant 1 has a much higher bone-to-bone contact area and commensurately little metal-to-bone interface. Unlike threaded titanium cages which have too large a diameter, the spinal implant 1 can be relatively easily used in "tall" disc spaces. The spinal implant 1 can also be used in either a "stand alone" manner in collapsed discs or as an adjunct to a 360-degree fusion providing cervical column support.

The spinal implant 1 offers safety advantages over conventional-used threaded cages. The spinal implant 1 is also easier to implant, avoiding the tubes necessary to insert some conventional cages, and easier to center. Without having to put a tube into the disc space, the vein can be visualized by both the spine surgeon and the vascular surgeon while working with the spinal implant 1. Anterior-posterior (AP) fluoroscopy can easily be achieved with trial before implanting the spinal implant 1, ensuring proper placement. The smooth and rounded edges 54 of the spinal implant 1 facilitate insertion and enhance safety. In highly preferred aspects, no reaming of the endplate, which weakens the interface between the endplate and the cage, is necessary for the spinal implant 1. Therefore, no reamers or taps are generally needed to insert and position the spinal implant 1.

Cages made of PEEK or carbon fiber cannot withstand the high impact forces needed for implantation, especially in a collapsed disc or spondylolisthesis situation, without secondary instruments. In contrast, the spinal implant 1 avoids the need for secondary instruments. Moreover, relative to PEEK or carbon fiber cages, the spinal implant 1 provides better distraction through endplate sparing and being designed to be implanted on the apophysis (the bony protuberance of the human spine). The titanium of the top surface 10 and 210 and the bottom plate 20 of the spinal implant 1 binds to bone with a mechanical (knawling) and a chemical (a hydrophilic) bond. In contrast, bone repels PEEK and such incompatibility can lead to locked pesudoarthrosis.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Figure 8:
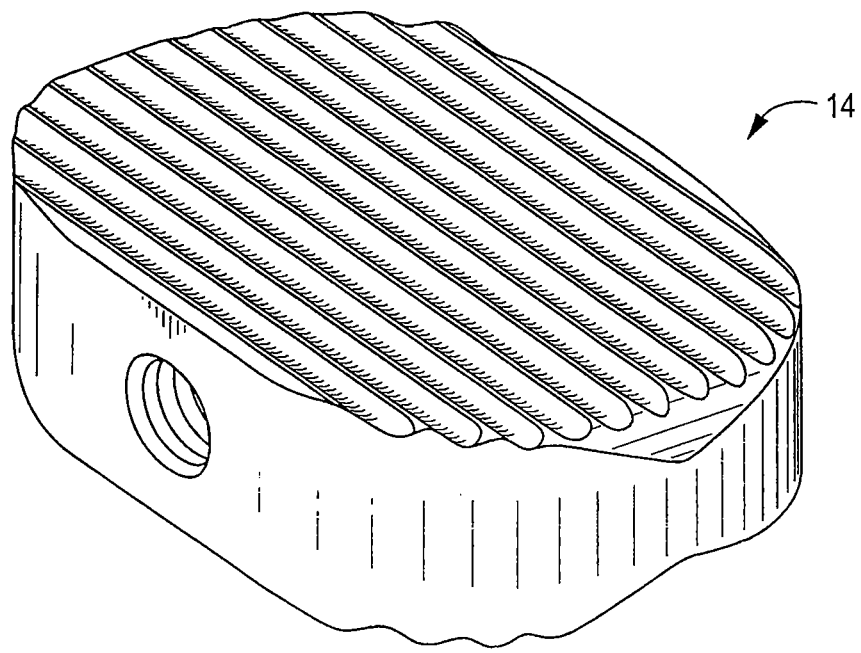
FIG. 8 shows an exemplary rasp used during certain methods of implantation.

FIG. 8 shows one example of a rasp 14 that may be used during certain methods of implantation. Typically, either a 32 mm or a 36 mm rasp 14 may used. A single rasp 14 may be used during implantation to remove a minimal amount of bone. A lateral c-arm fluoroscopy can be used to follow insertion of the rasp 14 in the posterior disc space. The smallest height rasp 14 that touches both endplates (e.g., the superior and inferior endplates) is first chosen. After the disc space is cleared of all soft tissue and cartilage, distraction is then accomplished by using distractors (also called implant trials or distraction plugs). It is usually possible to distract 2-3 mm higher than the rasp 14 that is used because the disk space is elastic.

FIGS. 12A-E show another embodiment of a rasp 101 that may be used during certain methods of implantation. Typically, either a 32 mm or a 36 mm rasp 101 may used. A single rasp 101 may be used during implantation to remove a minimal amount of bone. A lateral c-arm fluoroscopy can be used to follow insertion of the rasp 101 in the posterior disc space. The smallest height rasp 101 that touches both endplates (e.g., the superior and inferior endplates) is first chosen. After the disc space is cleared of all soft tissue and cartilage, distraction is then accomplished by using distractors (also called implant trials or distraction plugs). It is usually possible to distract 2-3 mm higher than the rasp 101 that is used because the disk space is elastic.

Figure 12A:
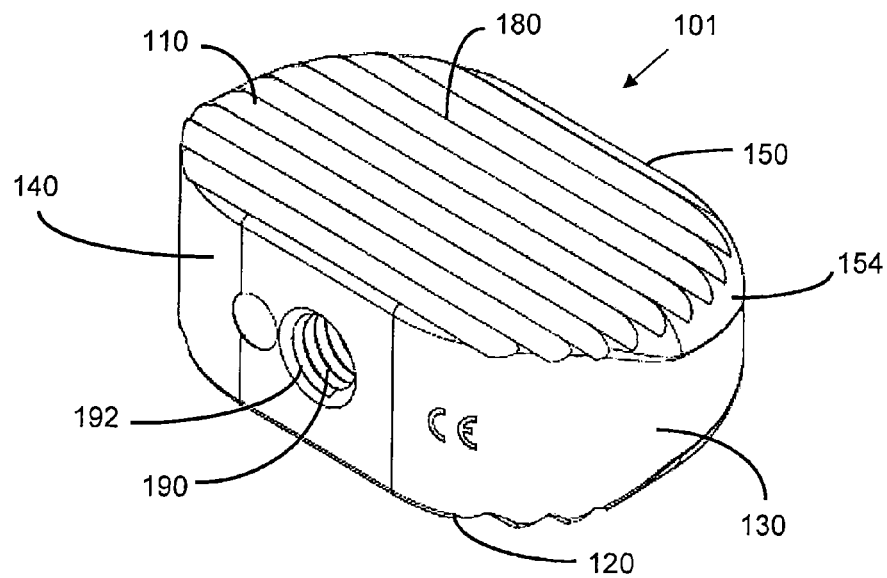
FIG. 12A shows an anterior, isometric view of an embodiment of a rasp instrument to assist in preparation of the bone for accommodation of the interbody spinal implant shown in FIG. 9.
Figure 12B:
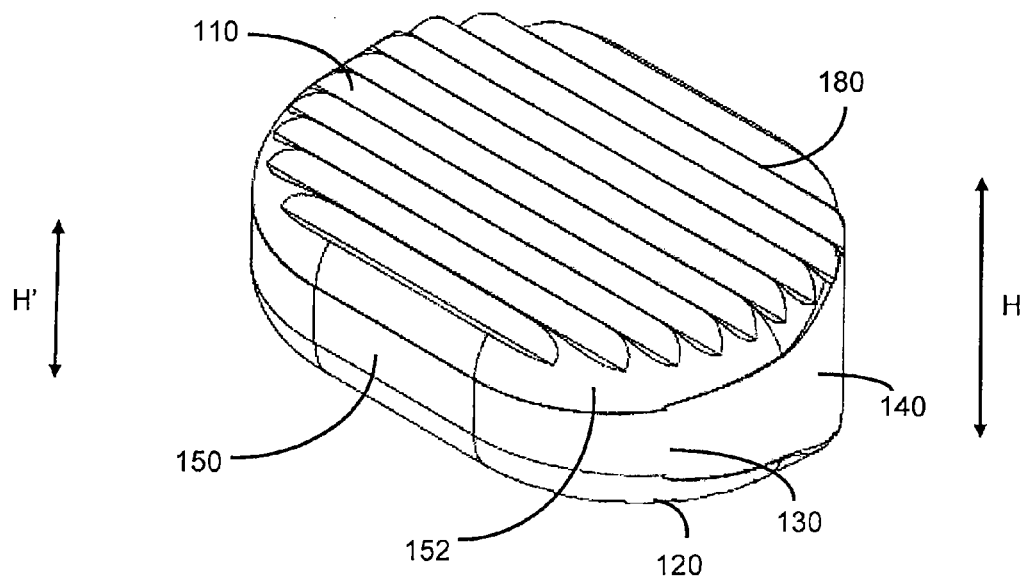
FIG. 12B shows a posterior, isometric view of an embodiment of a rasp instrument to assist in preparation of the bone for accommodation of the interbody spinal implant shown in FIG. 9.

In one embodiment as shown in FIG. 12A and FIG. 12B, the rasp 101 comprises a top surface 110, a bottom surface 120, opposing lateral sides 130, and opposing anterior 140 and posterior 150 portions. The anterior portion 140 may comprise an instrument connection 190 (FIG. 12E), to allow the user to connect an instrument (not shown) to the rasp 101, for example, to move the rasp 101 during tissue clearing. The instrument connection 190 may comprise screw threads 192 to facilitate the connection.

Figure 12C:
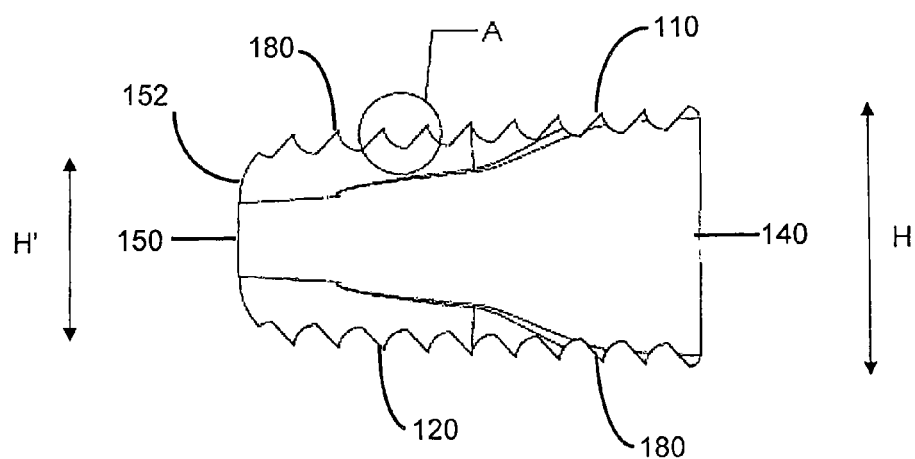
FIG. 12C shows a side view of the rasp instrument shown in FIG. 12A and FIG. 12B.

The anterior portion 140 of the rasp 101 is preferably generally greater in height than the opposing posterior portion 150. Accordingly, the rasp 101 may comprise a lordotic-angle, e.g., may be wedge-shaped. Thus, for example, the anterior portion 140 of the rasp 101 may comprise a height H that is larger than the height H' of the posterior portion 150, as shown in FIG. 12B and FIG. 12C. The anterior portion 140 height H and posterior portion 150 height H' may vary, and may vary independently, in order to accommodate different lordotic angles.

The anterior portion 140 height H and the posterior portion 150 height H' may each independently be from about 5 mm to about 75 mm. In preferred aspects, the height H and the height H' may each independently be from about 8 mm to about 20 mm. Thus, for example, either the height H or the height H' may be selected from about 5 mm, about 8 mm, about 10 mm, about 12 mm, about 14 mm, about 16 mm, about 18 mm, about 20 mm, about 22 mm, about 24 mm, about 25 mm, about 28 mm, about 30 mm, about 33 mm, about 35 mm, about 38 mm, about 40 mm, about 43 mm, about 45 mm, about 48 mm, about 50 mm, about 53 mm, about 55 mm, about 58 mm, about 60 mm, about 63 mm, about 65 mm, about 68 mm, about 70 mm, about 75 mm, or about 80 mm.

The difference in the anterior portion 140 height H and the posterior portion 150 height H' may result in a lordotic angle of from about 3 degrees to about 15 degrees, from the horizontal plane of the rasp 101. In preferred aspects, the rasp 101 comprises an angle of about 4 degrees, about 5 degrees, about 6 degrees, about 7 degrees, about 8 degrees, about 9 degrees, about 10 degrees, about 11 degrees, or about 12 degrees. Angles of lordosis of about 4 degrees, about 6 degrees, about 7 degrees, or about 12 degrees are highly preferred.

The posterior portion 150 of the rasp 101 may also be highly radiused. Thus, the posterior portion 150 may have a generally blunt nosed profile, including a generally rounded profile, for example, as shown in FIG. 12B. Posterior portion edges 154 of the rasp 101, including the top and bottom edges and lateral corner edges of the posterior portion 150, are preferably generally rounded, and are preferably smooth.

Figure 12D:
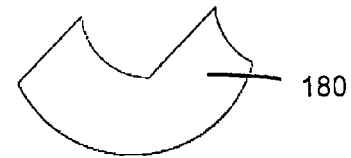
FIG. 12D shows an enlarged view of the rasping teeth of the rasp instrument shown in FIG. 12C.
Figure 12E:
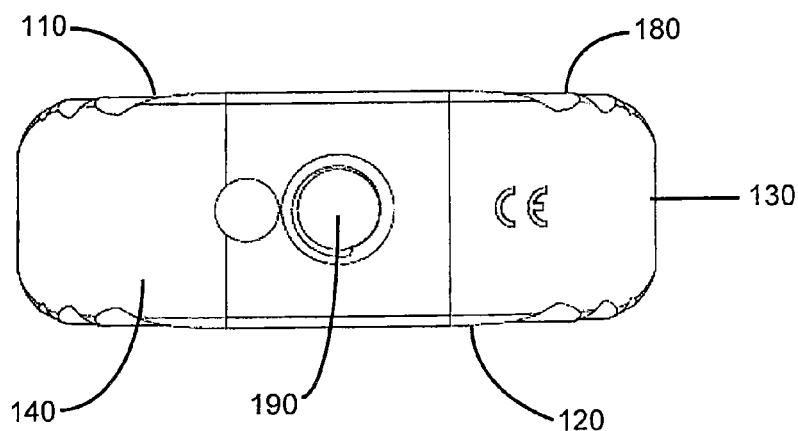
FIG. 12E shows a front-on view of the anterior portion of the rasp instrument shown in FIG. 12A and FIG. 12B.

The rasp 101 comprises a plurality of teeth 180 extending laterally across either or both of the top portion 110 and the bottom portion 120 of the rasp 101. As shown in FIG. 12C, each tooth 180 includes a sharp tip that faces the anterior portion 140 of the rasp 101. Thus, in some aspects, the tip of each tooth 180 is in a rearward-facing direction. FIG. 12D shows an enlarged, side view of two teeth 180 from the top portion 110 of the rasp 101, as enlarged from the position A shown in FIG. 12C.

Figure 7:
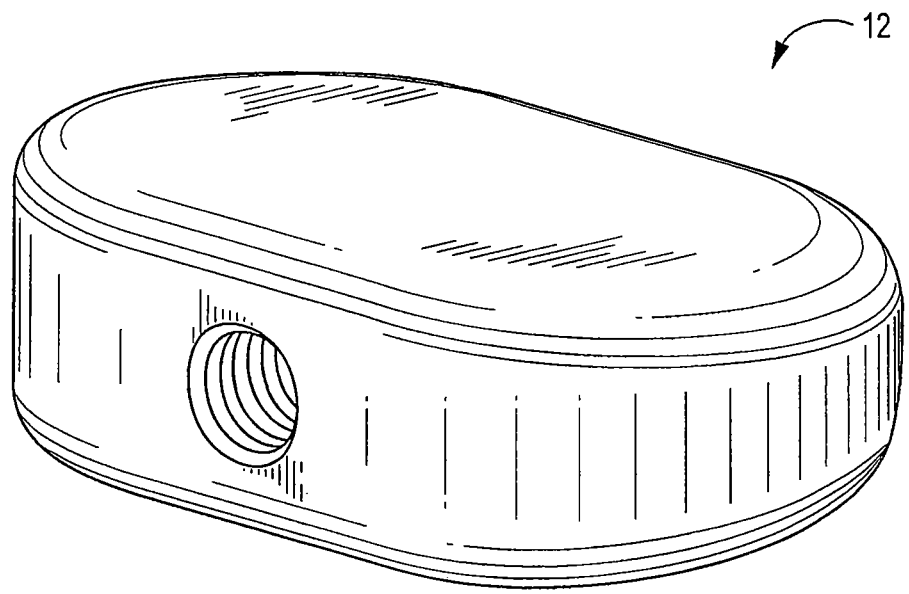
FIG. 7 shows an exemplary distractor used during certain methods of implantation.

FIG. 7 shows an exemplary distractor 12 used during certain methods of implantation. The implant trials, or distractors 12, are solid polished blocks which have a peripheral geometry identical to that of the implant 1. These distractor blocks may be made in various heights to match the height of the implant 1. The disc space is adequately distracted by sequentially expanding it with distractors 12 of progressively increasing heights. The distractor 12 is then left in the disc space and the centering location may be checked by placing the c-arm back into the AP position. If the location is confirmed as correct (e.g., centered), the c-arm is turned back into the lateral position. The spinal implant 1 is filled with autologous bone graft or bone graft substitute. The distractor 12 is removed and the spinal implant 1 is inserted under c-arm fluoroscopy visualization. In some aspects, the process according to the invention does not use a secondary distractor; rather, distraction of the disc space is provided by the spinal implant 1 itself (i.e., the implant 1 itself is used as a distractor).

FIGS. 13A-D show an exemplary trial instrument/distractor 201 that may be used during certain methods of implantation. The trial instrument 201 may be used as a distraction tool, and preferably has a peripheral geometry identical to that of the implant 1. The trial instrument 201 may be made in various heights, for example, to match the height H of the anterior portion 40 of the implant 1. The disc space may be distracted by expanding it with trial instrument 201. The trial instrument 201 may be left in the disc space and the centering location may be checked by placing the c-arm back into the AP position. If the location is confirmed as correct (e.g., centered), the c-arm is turned back into the lateral position. The spinal implant 1 is filled with autologous bone graft or bone graft substitute. The trial instrument 201 is removed and the spinal implant 1 is inserted under c-arm fluoroscopy visualization. In some aspects, the process according to the invention does not use a secondary distractor; rather, distraction of the disc space is provided by the spinal implant 1 itself (i.e., the implant 1 itself is used as a distractor).

Figure 13A:
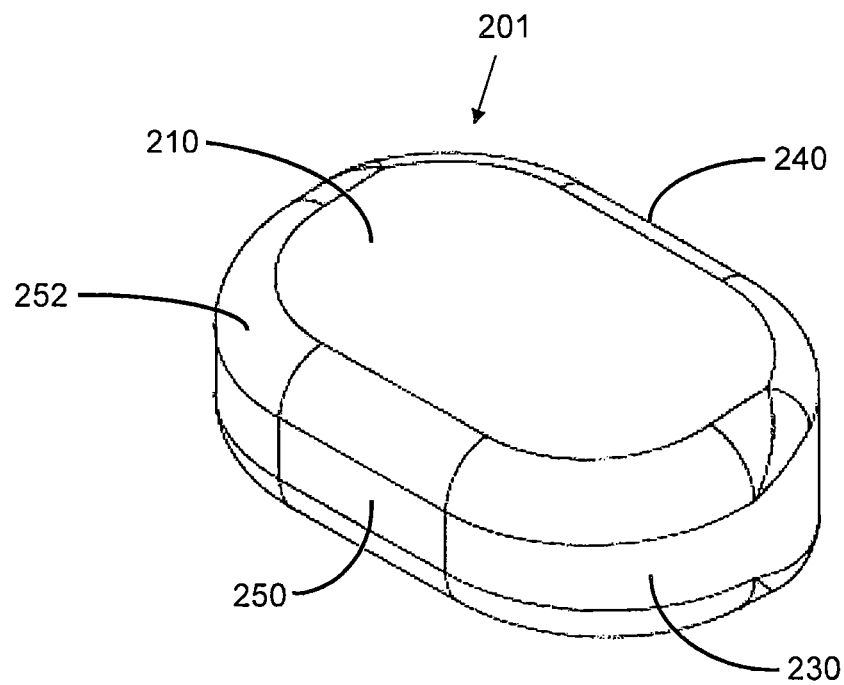
FIG. 13A shows a posterior, isometric view of a trial instrument to assist in sizing the implant during surgery.
Figure 13B:
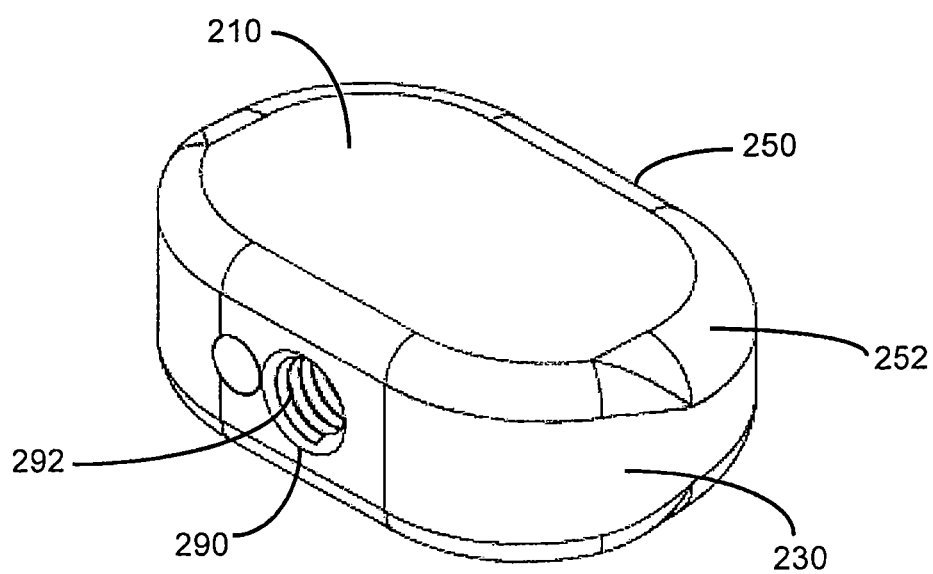
FIG. 13B shows an anterior, isometric view of a trial instrument to assist in sizing the implant during surgery.

In one embodiment as shown in FIG. 13A and FIG. 13B, the trial instrument 201 comprises a top surface 210, a bottom surface 220, opposing lateral sides 230, and opposing anterior 240 and posterior 250 portions. The anterior portion 240 may comprise an instrument connection 290 (FIG. 13B, FIG. 13D), to allow the user to connect an instrument (not shown) to the trial instrument 201, for example, to reposition or remove the trial instrument 201. The instrument connection 290 may comprise screw threads 292 to facilitate the connection.

Figure 13C:
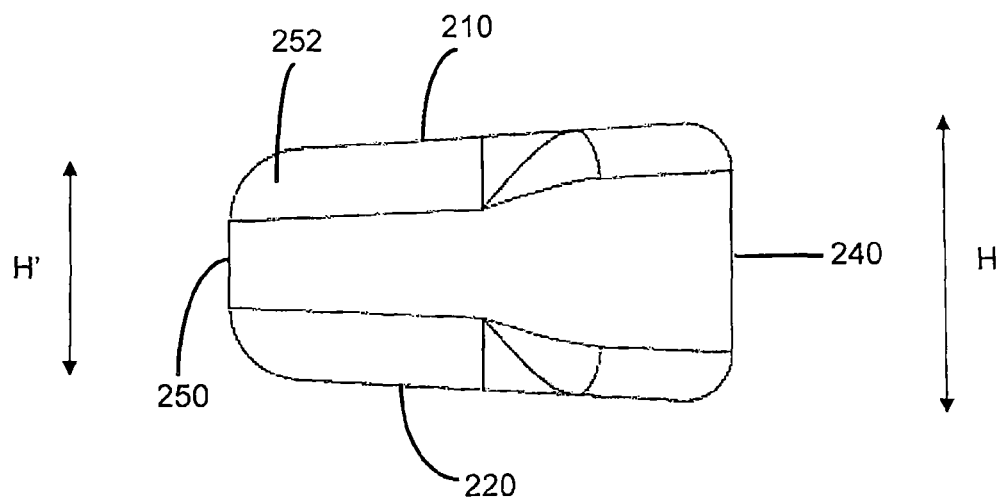
FIG. 13C shows a side view of the trial instrument shown in FIG. 13A and FIG. 13B; and, FIG. 13D shows a front-on view of the anterior portion of the trial instrument shown in FIG. 13A and FIG. 13B.
Figure 13D:
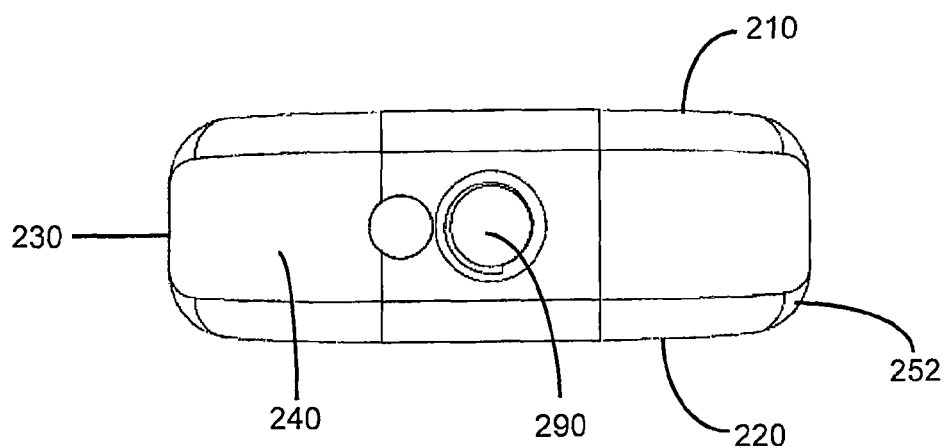

The anterior portion 240 of the trial instrument 201 is preferably generally greater in height than the opposing posterior portion 250. Accordingly, the trial instrument 201 may comprise a lordotic-angle, e.g., may be wedge-shaped. Thus, for example, the anterior portion 240 of the trial instrument 201 may comprise a height H that is larger than the height H' of the posterior portion 250, as shown in FIG. 13C. The anterior portion 240 height H and posterior portion 250 height H' may vary, and may vary independently, in order to accommodate different lordotic angles.

The anterior portion 240 height H and the posterior portion 250 height H' may each independently be from about 5 mm to about 75 mm. In preferred aspects, the height H and the height H' may each independently be from about 8 mm to about 20 mm. Thus, for example, either the height H or the height H' may be selected from about 5 mm, about 8 mm, about 10 mm, about 12 mm, about 14 mm, about 16 mm, about 18 mm, about 20 mm, about 22 mm, about 24 mm, about 25 mm, about 28 mm, about 30 mm, about 33 mm, about 35 mm, about 38 mm, about 40 mm, about 43 mm, about 45 mm, about 48 mm, about 50 mm, about 53 mm, about 55 mm, about 58 mm, about 60 mm, about 63 mm, about 65 mm, about 68 mm, about 70 mm, about 75 mm, or about 80 mm.

The difference in the anterior portion 240 height H and the posterior portion 250 height H' may result in a lordotic angle of from about 3 degrees to about 15 degrees, from the horizontal plane of the trial instrument 201. In preferred aspects, the trial instrument 201 comprises an angle of about 4 degrees, about 5 degrees, about 6 degrees, about 7 degrees, about 8 degrees, about 9 degrees, about 10 degrees, about 11 degrees, or about 12 degrees. Angles of lordosis of about 4 degrees, about 6 degrees, about 7 degrees, or about 12 degrees are highly preferred.

The posterior portion 250 of the trial instrument 201 may also be highly radiused. Thus, the posterior portion 250 may have a generally blunt nosed profile, including a generally rounded profile, for example, as shown in FIG. 13A. Posterior portion edges 254 of the trial instrument 201, including the top and bottom edges and lateral corner edges of the posterior portion 250, are preferably generally rounded, and are preferably smooth.

Use of a rasp 14 as shown in FIG. 8 or a rasp 101 as shown in FIGS. 12A-E preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant into the vertebral body.

Preferred embodiments of the present surgical method minimize endplate bone removal on the whole, while still allowing for some removal along the vertebral endplate far lateral edges where the subchondral bone is thickest. Still further, certain embodiments of the interbody spinal implant 1 include smooth, rounded, and highly radiused posterior portions and lateral sides which may minimize extraneous bone removal for endplate preparation and reduce localized stress concentrations. Thus, interbody surgical implant 1 and methods of using it are particularly useful in preserving the natural arch of the vertebral endplate and minimizing the chance of implant subsidence.

Because the endplates are spared during the process of inserting the spinal implant 1, hoop stress of the inferior and superior endplates is maintained. Spared endplates allow the transfer of axial stress to the apophasis. Endplate flexion allows the bone graft placed in the interior of the spinal implant 1 to accept and share stress transmitted from the endplates. In addition, spared endplates minimize the concern that BMP might erode the cancellous bone.

Interbody spinal implant 1 is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, those embodiments having a surface roughened topography 80 may lessen the risk of excessive bone removal during distraction as compared to implants having teeth, ridges, or threads currently known in the art even in view of a press-fit surgical distraction method. Nonetheless, once implanted, the interbody surgical implant 1 may provide secure seating and prove difficult to remove. Thus, certain embodiments of the interbody spinal implant 1 may maintain a position between the vertebral endplates due, at least in part, to resultant annular tension attributable to press-fit surgical implantation and, post-operatively, improved osteointegration at the top surface 10, the bottom surface 20, or both top and bottom surfaces.

Surgical implants and methods tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1 may be used as the final distractor and thus maintain the relative position of the vertebrae without the need for secondary instrumentation.

Certain embodiments collectively comprise a family of implants, each having a common design philosophy. These implants and the associated surgical technique have been designed to address at least the ten, separate challenges associated with the current generation of traditional anterior spinal fusion devices listed above in the Background section of this document.

Embodiments of the invention allow end-plate preparation with custom-designed rasps 14, 101. These rasps 14, 101 preferably have a geometry matched with the geometry of the implant. The rasps 14, 101 conveniently remove cartilage from the endplates and remove minimal bone, only in the postero-lateral regions of the vertebral end-plates. It has been reported in the literature that the end-plate is the strongest in postero-lateral regions.

After desired annulotomy and discectomy, embodiments of the invention first adequately distract the disc space by inserting (through impaction) and removing sequentially larger sizes of very smooth distractors 12 or by inserting and removing a trial instrument 201, which respectively have been size matched with the size of the available implant 1. Once adequate distraction is achieved, the surgeon prepares the end-plate with a rasp 14, 101. There is no secondary instrumentation required to keep the disc space distracted while the implant 1 is inserted, as the implant 1 has sufficient mechanical strength that it is impacted into the disc space. In fact, the height of the implant 1 is preferably about 1 mm greater than the height of the rasp 14, 101 used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1 is designed such that all the impact loads are applied only to the titanium part of the construct. Thus, the implant 1 has adequate strength to allow impact. The sides of the implant 1 have smooth surfaces to allow for easy implantation and, specifically, to prevent binding of the implant 1 to soft tissues during implantation.

The invention encompasses a number of different implant 1 configurations, including a one-piece, titanium-only implant and a composite implant formed of top and bottom plates (components) made out of titanium. The surfaces exposed to the vertebral body are dual acid etched to allow for bony in-growth over time, and to provide resistance against expulsion. The top and bottom titanium plates are assembled together with the implant body that is injection molded with PEEK. The net result is a composite implant that has engineered stiffness for its clinical application. The axial load is borne by the PEEK component of the construct.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1 designed according to certain embodiments allows the vertebral end-plate to deflect and allows healing of the bone graft into fusion.

In some aspects, certain faces of the implant 1 have sharp edges 8, 9. These edges 8, 9 tend to "dig" into the end-plates slightly and help to resist expulsion. The edges 8, 9 may be present on the top surface 10 of the implant 1, the bottom surface 20 of the implant 1, or both surfaces of the implant 1.

The top and bottom surfaces of the implant are made out of titanium and are dual acid etched. The dual acid etching process creates a highly roughened texture on these surfaces, which generates tremendous resistance to expulsion. The width of these dual acid etched surfaces is very broad and creates a large area of contact with the vertebral end-plates, further increasing the resistance to expulsion.

The implant 1 according to certain embodiments of the invention has a large foot-print, and offers several sizes. Because there is no secondary instrument required to maintain distraction during implantation, all the medial-lateral (ML) exposure is available as implantable ML width of the implant. This feature allows the implant to contact the vertebral end-plates at the peripheral apophyseal rim, where the end-plates are the strongest and least likely to subside.

Further, there are no teeth on the top and bottom surfaces (teeth can create stress risers in the end-plate, encouraging subsidence). Except for certain faces, all the implant surfaces have heavily rounded edges, creating a low stress contact with the end-plates. The wide rim of the top and bottom surfaces, in contact with the end-plates, creates a low-stress contact due to the large surface area. Finally, the implant construct has an engineered stiffness to minimize the stiffness mismatch with the vertebral body which it contacts.

The implant 1 according to certain embodiments of the invention has a large foot-print. In addition, titanium provides high strength for a small volume. In combination, the large foot-print along with the engineered use of titanium allows for a large volume of bone graft to be placed inside the implant.

It is believed that an intact vertebral end-plate deflects like a diaphragm under axial compressive loads generated due to physiologic activities. If a spinal fusion implant is inserted in the prepared disc space via a procedure which does not destroy the end-plate, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1 according to certain embodiments of the invention allows the vertebral end-plate to deflect and facilitates healing of the bone graft into fusion.

The top and bottom surfaces of the implant 1 according to certain embodiments of the invention are made of titanium and are dual acid etched. The dual acid etched surface treatment of titanium allows in-growth of bone to the surfaces. Hence, the implant 1 is designed to incorporate with the vertebral bone over time. It may be that the in-growth happens sooner than fusion. If so, there may be an opportunity for the patients treated with the implant 1 to return to normal activity levels sooner than currently recommended by standards of care.

Even the titanium-only embodiment of the invention has been designed with large windows to allow for radiographic evaluation of fusion, both through AP and lateral X-rays. A composite implant minimizes the volume of titanium, and localizes it to the top and bottom surfaces. The rest of the implant is made of PEEK which is radiolucent and allows for free radiographic visualization.

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed:

1. An interbody spinal implant generally oval-shaped in transverse cross-section and comprising:
   a top surface, a bottom surface, opposing lateral sides, and opposing anterior and posterior portions, the posterior portion defining a leading end for insertion first into a disc space, having a generally rounded nose profile, and having a shorter height than the anterior portion thereby defining a lordotic angle for aligning spine of a patient;
   a roughened surface topography adapted to grip bone and inhibit migration of the implant on at least a portion of the top surface, the bottom surface, or both the top and bottom surfaces;
   generally rounded and blunt intersections defined along the entire lengths between the top surface and the posterior portion, the bottom surface and the posterior portion, the top surface and the lateral sides, and the bottom surface and the lateral sides;
   a sharp edge between the top and bottom surfaces and the anterior portion to resist pullout;
   the spinal implant being substantially hollow and having a centrally disposed vertical aperture (a) extending from the top surface to the bottom surface, (b) defining a transverse rim with a varying width or thickness, and (c) having a maximum width at its center, between the opposing lateral sides, and tapering inwardly from the center to each of its ends, one end proximate the anterior portion and the other end proximate the posterior portion.

2. The spinal implant of claim 1, wherein the spinal implant is comprised of titanium.

3. The spinal implant of claim 1, wherein the spinal implant is comprised of a non-metal selected from the group consisting of polyetherether-ketone, hedrocel, and ultra-high molecular weight polyethylene.

4. The spinal implant of claim 1, wherein the spinal implant is comprised of a composite formed, in part, of titanium and, in part, of a non-metal selected from the group consisting of polyetherether-ketone, hedrocel, and ultra-high molecular weight polyethylene.

5. The spinal implant of claim 1, wherein the anterior portion is substantially flat and adapted to receive impact from an implant tool.

6. The spinal implant of claim 1, further comprising bone graft material disposed in the substantially hollow center and adapted to facilitate the formation of a solid fusion column within the spine.

7. The spinal implant of claim 6, wherein the bone graft material is cancellous autograft bone, allograft bone, demineralized bone matrix (DBM), porous synthetic bone graft substitute, bone morphogenic protein (BMP), or a combination thereof.

8. The spinal implant of claim 1, further comprising a wall closing at least one of the opposing anterior and posterior portions adapted to contain bone graft material.

9. The spinal implant of claim 1, wherein the anterior portion has an opening for achieving one or more of the following functions: being adapted to engage a delivery device, facilitating delivery of bone graft material to the substantially hollow center, enhancing visibility of the implant, and providing access to the bone graft material.

10. The spinal implant of claim 1, wherein the spinal implant is adapted to be inserted into a prepared disc space via a procedure which does not destroy the vertebral end-plates or to contact the vertebral end-plates only peripherally, allowing the intact vertebral end-plates to deflect like a diaphragm under axial compressive loads generated due to physiologic activities and pressurize the bone graft material disposed inside the spinal implant.

11. The spinal implant of claim 1, wherein the generally rounded and blunt intersections comprise radiused portions with a radius oriented along a plane from the top surface to the bottom surface.

12. The spinal implant of claim 1, wherein the sharp edge comprises an anti-expulsion edge angle of from 80 degrees to 100 degrees.

13. The spinal implant of claim 1, wherein the vertical aperture defines a second sharp edge proximate to the posterior portion of the implant.

14. A system for implanting a spinal implant into a patient in need thereof, comprising the spinal implant of claim 1 and a distractor.

15. The system of claim 14, wherein the distractor comprises a top surface, a bottom surface, opposing lateral sides, and opposing anterior and posterior portions, the posterior portion defining a leading end for insertion first into a disc space, having a generally rounded nose profile, and having a shorter height than the anterior portion thereby defining a lordotic angle.

16. The system of claim 15, wherein the distractor is adapted to be inserted into a prepared disc space via a procedure which does not destroy the vertebral end-plates or to contact the vertebral end-plates only peripherally.

17. The system of claim 14, further comprising a rasp.

18. The system of claim 17, wherein the rasp comprises a top surface, a bottom surface, opposing lateral sides, opposing anterior and posterior portions, and a plurality of teeth having a tip facing the anterior portion, the teeth extending laterally across the top surface, the bottom surface, or the top and bottom surface of the rasp, the posterior portion defining a leading end for insertion first into a disc space, having a generally rounded nose profile, and having a shorter height than the anterior portion thereby defining a lordotic angle.

19. The system of claim 14, further comprising an implant holder capable of engaging an opening on the anterior portion of the spinal implant.

20. The system of claim 14, further comprising a bone graft material.

21. The system of claim 20, wherein the bone graft material is cancellous autograft bone, allograft bone, demineralized bone matrix (DBM), porous synthetic bone graft substitute, bone morphogenic protein (BMP), or a combination thereof.

22. A method for implanting a spinal implant while preserving vertebral endplates, comprising implanting the spinal implant of claim 1 into a patient in need thereof such that the vertebral endplates remain substantially undamaged during the implanting step.

23. The method of claim 22, further comprising, prior to implanting the spinal implant, rasping the space between the vertebrae of the patient using a rasp having a plurality of teeth having a rearward-facing tip, with substantially no rasping of the bone.

24. The method of claim 22, further comprising distracting the space between the vertebrae of the patient before implanting the spinal implant.

* * * * *